United States Patent
Yasuda et al.

(10) Patent No.: US 10,494,338 B2
(45) Date of Patent: Dec. 3, 2019

(54) PROSTAGLANDIN DERIVATIVE

(71) Applicants: AGC INC., Chiyoda-ku (JP); NIPPON ZOKI PHARMACEUTICAL CO., LTD., Osaka-shi (JP)

(72) Inventors: Arata Yasuda, Chiyoda-ku (JP); Yasushi Matsumura, Chiyoda-ku (JP); Kazuyoshi Sawada, Kato (JP); Hiroyoshi Nanba, Kato (JP); Kazuki Taguchi, Kato (JP)

(73) Assignees: AGC INC., Chiyoda-ku (JP); NIPPON ZOKI PHARMACEUTICAL CO., LTD., Osaka-shi (JP)

( * ) Notice: Subject to any disclaimer, the term of this patent is extended or adjusted under 35 U.S.C. 154(b) by 0 days.

(21) Appl. No.: 16/099,929

(22) PCT Filed: May 9, 2017

(86) PCT No.: PCT/JP2017/017489
§ 371 (c)(1),
(2) Date: Nov. 8, 2018

(87) PCT Pub. No.: WO2017/195762
PCT Pub. Date: Nov. 16, 2017

(65) Prior Publication Data
US 2019/0135743 A1    May 9, 2019

(30) Foreign Application Priority Data
May 9, 2016 (JP) ................. 2016-094196

(51) Int. Cl.
| C07C 405/00 | (2006.01) |
| A61P 9/08 | (2006.01) |
| A61P 9/10 | (2006.01) |
| A61P 9/12 | (2006.01) |

(52) U.S. Cl.
CPC .......... *C07C 405/0016* (2013.01); *A61P 9/08* (2018.01); *A61P 9/10* (2018.01); *A61P 9/12* (2018.01); *C07C 405/0041* (2013.01)

(58) Field of Classification Search
None
See application file for complete search history.

(56) References Cited

U.S. PATENT DOCUMENTS

| 3,931,296 A | 1/1976 | Hayashi et al. |
| 4,052,512 A | 10/1977 | Hayashi et al. |
| 4,073,934 A | 2/1978 | Skuballa et al. |
| 4,235,930 A | 11/1980 | Skuballa et al. |
| 4,294,849 A | 10/1981 | Hayashi et al. |
| 5,449,815 A | 9/1995 | Sato et al. |
| 5,639,899 A | 6/1997 | Sato et al. |
| 6,455,584 B1 | 9/2002 | Sato et al. |

FOREIGN PATENT DOCUMENTS

| JP | 50-71649 A | 6/1975 |
| JP | 50-116452 A | 9/1975 |
| JP | 51-131860 A | 11/1976 |
| JP | 52-85151 A | 7/1977 |
| JP | 53-149954 A | 12/1978 |
| JP | 54-12352 A | 1/1979 |
| JP | 55-100360 A | 7/1980 |
| JP | 6-128158 A | 5/1994 |
| JP | 2002-155046 A | 5/2002 |
| WO | WO 92/18472 | 10/1992 |
| WO | WO 00/61550 | 10/2000 |
| WO | WO 01/66518 A1 | 9/2001 |

OTHER PUBLICATIONS

D. D Van Dorp, "Recent Developments in the Biosynthesis and the Analyses of Prostaglandins" Annals. New York Academy of Sciences, vol. 180, 1971, pp. 181-199.
"The Synthesis of $\Delta^2$-Prostaglandins" Prostaglandins, vol. 8, No. 4, Nov. 25, 1974, pp. 341-344.
International Search Report dated Jul. 4, 2017 in PCT/JP2017/017489 filed May 9, 2017.

*Primary Examiner* — Kamal A Saeed
(74) *Attorney, Agent, or Firm* — Oblon, McClelland, Maier & Neustadt, L.L.P.

(57) ABSTRACT

The present invention relates to a novel prostaglandin derivative having an alkynyl group on ω-chain, particularly, a novel prostaglandin derivative having a double bond at the 2-position and an alkynyl group on the ω-chain and a medicament containing the compound as an active ingredient.
According to the present invention, a compound represented by the formula (1) or a pharmaceutically acceptable salt thereof;

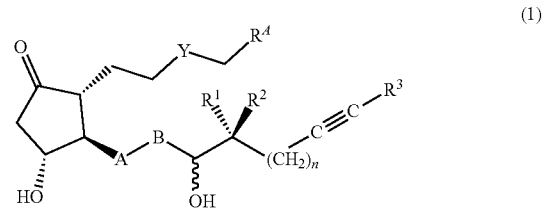

(1)

wherein each symbol is as defined in the present specification, or a cyclodextrin clathrate compound thereof, and a medicament containing the compound as an active ingredient, particularly, a medicament for the prophylaxis or treatment of a blood flow disorder associated with spinal canal stenosis or chronic arterial occlusion, can be provided.

20 Claims, No Drawings

PROSTAGLANDIN DERIVATIVE

TECHNICAL FIELD

The present invention relates to a novel prostaglandin derivative having an alkynyl group on the ω-chain of a prostaglandin, a pharmaceutically acceptable salt thereof, or a cyclodextrin clathrate compound thereof, particularly, a novel prostaglandin derivative having a double bond at the 2-position of a prostaglandin and an alkynyl group on the ω-chain. In addition, the present invention relates to a medicament containing at least one of the prostaglandin derivative, a pharmaceutically acceptable salt thereof, and a cyclodextrin clathrate compound thereof as an active ingredient, particularly a medicament for the prophylaxis or treatment of a blood flow disorder.

BACKGROUND ART

Peripheral arterial occlusive disease is a disease in which the artery is constricted or occluded due to arteriosclerosis and thrombus formation, the periphery, particularly the lower limb, falls into an ischemic state, and exhibits symptoms such as cryaesthesia, intermittent claudication, pain, and ulcer or necrosis of lower limb. Improvement of the blood flow to the ischemic part is important for improving the lower limb symptoms, and treatments aiming at resuming blood circulation by drugs or physical methods are performed. Drugs having vasodilating action and platelet aggregation inhibiting action are used for drug therapy.

Peripheral vascular disease also manifests as atherosclerotic stenosis of the renal artery and can lead to renal ischemia and kidney dysfunction. Chronic diabetes can also lead to atherosclerosis and vascular complications involving large vessel, arteriole and capillary. Diabetic patients are at high risk of developing foot ulcer due to long-term complications of, for example, neuropathy and ischemia.

Spinal canal stenosis is a disease in which the spinal canal is narrowed due to hypertrophy degeneration of the spine and the ligamentum flavum that constitute the spinal canal and protrusion of the intervertebral disc, and neural tissues such as the nerve root and cauda equina are compressed and various symptoms are exhibited. Spinal canal stenosis is classified into extensive spinal canal stenosis, thoracic spinal canal stenosis, lumbar spinal canal stenosis and the like according to the narrow portion of the spinal canal. The symptoms thereof include lumbago, pain in the upper limb or lower limb, numbness and the like due to nerve compression. In particular, when the cauda equina is injured, lumbago, lower limb pain, numbness, weakness become severe during walking, and this symptom is called intermittent claudication.

Natural prostaglandins (hereinafter prostaglandin is to be indicated as PG) are a group of bicactive substances synthesized in vivo, and regulate cellular functions of each tissue of the body as a topical hormone having various physiological activities. In particular, PGE1s, which are one kind of natural PGs, have, for example, a vasodilating action, an angiogenesis action, a platelet aggregation suppressive action, and an epithelial regeneration promoting action. They are used as an antiplatelet agent, an agent for improving peripheral blood flow disorders and the like in the drug therapy of the above-mentioned diseases. While PGEs may be applicable to other indications, natural PGEs are extremely unstable chemically and metabolically. Thus, the development of PGE derivatives which are more stable and effective, and cause fewer side effects has been extensively studied.

A PG derivative having a double bond at the 2-position of PG and a production method thereof are reported in the following patent documents 1-5 and non-patent documents 1-2. In addition, a PG derivative having an alkynyl group in the ω-chain of PG and a production method thereof are reported in the following patent documents 6-7.

DOCUMENT LIST

Patent Documents

Patent document 1: JP-A-50-71649
Patent document 2: JP-A-50-116452
Patent document 3: JP-A-52-85151
Patent document 4: JP-A-53-149954
Patent document 5: JP-A-55-100360
Patent document 6: JP-A-51-131860
Patent document 7: JP-A-54-12352

Non-Patent Documents

Non-patent document 1: Ann. Acad. N. Y. Sci., 1971, vol. 180, p. 181.
Non-patent document 2: Prostaglandins, 1974, vol. 8, p. 341.

SUMMARY OF INVENTION

Problems to be Solved by the Invention

An object of the present invention is to provide a blood flow improving agent that can be administered orally, causes fewer side effects, shows higher safety, and is superior in the effectiveness and pharmacokinetic property, especially, a compound useful as a therapeutic agent for blood flow disorder and pain associated with spinal canal stenosis. Among the compounds described in the aforementioned documents, particularly, (2E)-7-((1R,2R,3R)-3-hydroxy-2-((1E,3S,5S)-3-hydroxy-5-methylnon-1-en-1-yl)-5-oxocyclopentyl)hept-2-enoic acid (limaprost) is a compound showing superior efficacy, and blood flow improving agents containing limaprost as an active ingredient are being used for the treatment of pain and cryaesthesia associated with thromboangiitis obliterans and spinal canal stenosis in the actual medical field. However, limaprost has side effects on the gastrointestinal tract, and there is still room for improvement in the blood flow increasing action and sustainability of drug efficacy. In particular, the side effect of limaprost that has a high smooth muscle contraction action and causes diarrhea is left as a problem to be solved. Therefore, the development of a PGE1 derivative having physiological activities similar to those of natural type, causing low side effects and having high sustainability has been intensively studied in and out.

However, a PG compound having a double bond at the 2-position of PG and an alkynyl group in the ω-chain has not been reported. Furthermore, synthetic examples, properties, physiological activities and the like of a PGE compound having a double bond at the 2-position of PG and a triple bond at the 18-position have not been reported.

In addition, synthetic examples, properties, physiological activities and the like of a PGE compound having a triple bond at the 18-position of PG and a cycloalkyl group on the end of the triple bond have not been reported at all.

Means of Solving the Problems

The present inventors have synthesized novel PG compounds and conducted studies in an attempt to clarify the properties and physiological activities. As a result, they have found that a compound represented by the following formula (1) (hereinafter sometimes to be indicated as compound (1)) or a pharmaceutically acceptable salt thereof (hereinafter compound (1) and a pharmaceutically acceptable salt thereof are sometimes to be generically indicated as "the compound of the present invention"), or cyclodextrin clathrate compounds thereof have superior properties and pharmacological action, and further that they are extremely superior compounds as blood flow improving agents, especially therapeutic drugs for blood flow disorder and pain associated with spinal canal stenosis, which resulted in the completion of the present invention.

Therefore, the present invention provides the following.
[1] A compound represented by the following formula (1) or a pharmaceutically acceptable salt thereof;

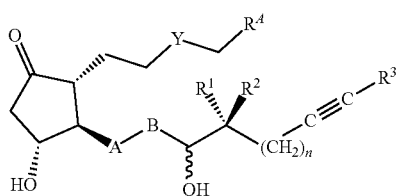

(1)

wherein
$R^4$ is —CH$_2$—CZ$^1$Z$^2$(COX) or —CH=CZ$^1$(COX), $Z^1$ and $Z^2$ are each independently a hydrogen atom or a fluorine atom, X is OR$^4$ or NR$^5$R$^6$, R$^4$ is a hydrogen atom, an alkyl group having 1-6 carbon atoms or a substituted alkyl group having 1-6 carbon atoms, R$^5$ is a hydrogen atom, an alkyl group having 1-6 carbon atoms or a substituted alkyl group having 1-6 carbon atoms, R$^6$ is a hydrogen atom, an alkyl group having 1-6 carbon atoms, a substituted alkyl group having 1-6 carbon atoms, an alkylsulfonyl group having 1-6 carbon atoms, a substituted alkylsulfonyl group having 1-6 carbon atoms, an arylsulfonyl group having 6-10 carbon atoms or a substituted arylsulfonyl group having 6-10 carbon atoms;

Y is CH$_2$, S or O;

A-B is a carbon-carbon single bond, a carbon-carbon double bond or a carbon-carbon triple bond;

a hydroxy group bonded by a wavy line is a hydroxy group having α-configuration, β-configuration or a mixed configuration of α-configuration and β-configuration;

$R^1$ and $R^2$ are each independently a hydrogen atom, an alkyl group having 1-3 carbon atoms or a substituted alkyl group having 1-3 carbon atoms;

n is an integer of 0-2;

$R^3$ is an alkyl group having 1-4 carbon atoms, a substituted alkyl group having 1-4 carbon atoms, a cycloalkyl group having 3-6 carbon atoms, a substituted cycloalkyl group having 3-6 carbon atoms, an aryl group having 6-10 carbon atoms or a substituted aryl group having 6-10 carbon atoms;

excluding 7-((1R,2R,3R)-3-hydroxy-2-((1E,3S,4RS)-3-hydroxy-4-methyloct-1-en-6-yn-1-yl)-5-oxocyclopentyl)heptanoic acid;

[2] the compound or a pharmaceutically acceptable salt thereof of [1], wherein Y is CH$_2$;
[3] the compound or a pharmaceutically acceptable salt thereof of [1] or [2], wherein $R^4$ is —CH=CZ$^1$(COX);
[4] the compound or a pharmaceutically acceptable salt thereof of [1] or [2], wherein $R^4$ is —CH$_2$—CZ$^1$Z$^2$(COX);
[5] the compound or a pharmaceutically acceptable salt thereof of any of [1]-[4], wherein n is 1;
[6] the compound or a pharmaceutically acceptable salt thereof of any of [1]-[5], wherein A-B is a carbon-carbon double bond;
[7] the compound of or a pharmaceutically acceptable salt thereof any of [1]-[6], wherein $R^1$ is a hydrogen atom and $R^2$ is an alkyl group having 1-3 carbon atoms;
[8] the compound or a pharmaceutically acceptable salt thereof of any of [1]-[7], wherein $R^3$ is an alkyl group having 2-3 carbon atoms or a cycloalkyl group having 3-5 carbon atoms;
[9] the compound or a pharmaceutically acceptable salt thereof of any of [1]-[8], wherein $R^3$ is a cycloalkyl group having 3-5 carbon atoms;
[10] the compound or a pharmaceutically acceptable salt thereof of any of [1]-[9], wherein X is OR$^4$;
[11] a cyclodextrin clathrate compound of the compound of any of [1]-[10] or a pharmaceutically acceptable salt thereof;
[12] a medicament comprising the compound or a pharmaceutically acceptable salt thereof of any of [1]-[10], or the cyclodextrin clathrate compound of [11] as an active ingredient;
[13] the medicament of [12], which is a prophylactic or therapeutic agent for a blood flow disorder;
[14] the medicament of [13], wherein the blood flow disorder is a blood flow disorder of nerve;
[15] the medicament of [14], wherein the blood flow disorder of nerve is a blood flow disorder associated with spinal canal stenosis;
[16] the medicament of [13], wherein the blood flow disorder is a blood flow disorder of peripheral artery, skin or brain;
[17] the medicament of [16], wherein the blood flow disorder of peripheral artery is a blood flow disorder associated with chronic arterial occlusion or pulmonary hypertension;
[18] the medicament of [16], wherein the blood flow disorder of skin is a blood flow disorder associated with pressure ulcer;
[19] the medicament of [16], wherein the blood flow disorder of brain is a blood flow disorder associated with suppression of recurrence after cerebral infarction;
[20] a method for prophylaxis or treatment of a blood flow disorder, comprising administering an effective amount of the compound or a pharmaceutically acceptable salt thereof of any of [1]-[10], or the cyclodextrin clathrate compound of [11] to a patient in need thereof;
[21] the method of [20], wherein the blood flow disorder is a blood flow disorder of nerve;
[22] the method of [21], wherein the blood flow disorder of nerve is a blood flow disorder associated with spinal canal stenosis;
[23] the method of [20], wherein the blood flow disorder is a blood flow disorder of peripheral artery, skin or brain;
[24] the method of [23], wherein the blood flow disorder of peripheral artery is a blood flow disorder associated with chronic arterial occlusion or pulmonary hypertension;
[25] the method of [23], wherein the blood flow disorder of skin is a blood flow disorder associated with pressure ulcer;

[26] the method of [23], wherein the blood flow disorder of brain is a blood flow disorder associated with suppression of recurrence after cerebral infarction;
[27] the compound or a pharmaceutically acceptable salt thereof of any of [1]-[10], or the cyclodextrin clathrate compound of [11] for use in the treatment of a blood flow disorder;
[28] the compound or a pharmaceutically acceptable salt thereof, or the cyclodextrin clathrate compound for use of [27], wherein the blood flow disorder is a blood flow disorder of nerve;
[29] the compound or a pharmaceutically acceptable salt thereof, or the cyclodextrin clathrate compound for use of [28], wherein the blood flow disorder of nerve is a blood flow disorder associated with spinal canal stenosis;
[30] the compound or a pharmaceutically acceptable salt thereof, or the cyclodextrin clathrate compound for use of [27], wherein the blood flow disorder is a blood flow disorder of peripheral artery, skin or brain;
[31] the compound or a pharmaceutically acceptable salt thereof, or the cyclodextrin clathrate compound for use of [30], wherein the blood flow disorder of peripheral artery is a blood flow disorder associated with chronic arterial occlusion or pulmonary hypertension;
[32] the compound or a pharmaceutically acceptable salt thereof, or the cyclodextrin clathrate compound for use of [30], wherein the blood flow disorder of skin is a blood flow disorder associated with pressure ulcer;
[33] the compound or a pharmaceutically acceptable salt thereof, or the cyclodextrin clathrate compound for use of [30], wherein the blood flow disorder of brain is a blood flow disorder associated with suppression of recurrence after cerebral infarction;
[34] use of the compound or a pharmaceutically acceptable salt thereof of any of [1]-[10], or the cyclodextrin clathrate compound of [11] in the manufacture of a prophylactic or therapeutic agent for a blood flow disorder;
[35] the use of [34], wherein the blood flow disorder is a blood flow disorder of nerve;
[36] the use of [35], wherein the blood flow disorder of nerve is a blood flow disorder associated with spinal canal stenosis;
[37] the use of [34], wherein the blood flow disorder is a blood flow disorder of peripheral artery, skin or brain;
[38] the use of [37], wherein the blood flow disorder of peripheral artery is a blood flow disorder associated with chronic arterial occlusion or pulmonary hypertension;
[39] the use of [37], wherein the blood flow disorder of skin is a blood flow disorder associated with pressure ulcer;
[40] the use of [37], wherein the blood flow disorder of brain is a blood flow disorder associated with suppression of recurrence after cerebral infarction and the like.

Effect of the Invention

The compound of the present invention has a very potent suppressive action on platelet aggregation in human and rat, and a superior blood flow increasing action when intravenously administered to rat in a cauda equine blood flow test. Thus, the compound is useful as a prophylactic or therapeutic agent for blood flow disorders.

In addition, the compound of the present invention is less susceptible to oxidative metabolism by PG dehydrogenase and has high metabolic stability since an alkyl group (particularly a methyl group) is bonded to the 16-position carbon atom adjacent to the 15-position hydroxy group of the PG skeleton. Consequently, the compound has a long half-life in blood and can maintain the effective blood concentration for a long time as compared to natural type PG compounds. The improved metabolic stability can markedly improve bioavailability of a drug containing the compound of the present invention.

DESCRIPTION OF EMBODIMENTS

The definition of each symbol in the formula (1) is described in detail below.

For naming of the compounds in the present specification, the IUPAC nomenclature is used in principle. To indicate the position of the PG skeleton, numerical numbering based on the prostanoic acid skeleton may sometimes be indicated as appropriate. In the present specification, a group in which a hydrogen atom of the alkyl group is substituted is also indicated as a substituted alkyl group. Similar indication is adopted for other groups as well. The "lower" means that the carbon number is 1-6, and 1-4 is preferable.

The "alkyl group" may be a linear chain or a branched chain. The alkyl group is preferably an alkyl group having 1-6 carbon atoms, particularly preferably an alkyl group having 1-4 carbon atoms. Examples of the alkyl group include methyl group, ethyl group, propyl group, isopropyl group, butyl group, isobutyl group, sec-butyl group, tert-butyl group, pentyl group, hexyl group.

The "alkenyl group" may be a linear chain or a branched chain. The alkenyl group is preferably an alkenyl group having 2-6 carbon atoms. Examples of the alkenyl group include vinyl group, allyl group, 1-propenyl group, isopropenyl group, 3-butenyl group, 3-pentenyl group, 4-hexenyl group and the like.

The "alkynyl group" may be a linear chain or a branched chain. The alkynyl group is preferably an alkynyl group having 2-6 carbon atoms. Examples of the alkynyl group include ethynyl group, 1-propynyl group, 2-propynyl group, 3-butynyl group, 3-pentynyl group, 4-hexynyl group and the like.

The "alkoxy group" is a group in which an oxygen atom is bonded to the terminal carbon atom of the alkyl group. The alkoxy group may be a linear chain or a branched chain. The alkoxy group is preferably an alkoxy group having 1-6 carbon atoms, and particularly preferably an alkoxy group having 1-4 carbon atoms. Examples of the alkoxy group include methoxy group, ethoxy group, propoxy group, butoxy group and the like.

The "halogen atom" is a fluorine atom, a chlorine atom, a bromine atom, or an iodine atom.

The "aryl group" is an aromatic hydrocarbon group, preferably an aryl group having 6-18 carbon atoms, particularly preferably an aryl group having 6-10 carbon atoms. Examples of the aryl group include phenyl group, naphthyl group, anthryl group and the like, and phenyl group is particularly preferable.

The "aralkyl group" is an alkyl group to which an aryl group is bonded. The aryl group of the aralkyl group is preferably an aryl group having 6-10 carbon atoms, particularly preferably a phenyl group. The alkyl group of the aralkyl group is preferably an alkyl group having 1-4 carbon atoms. Examples of the aralkyl group include benzyl group, benzhydryl group, trityl group, phenylethyl group and the like.

The "cycloalkyl group" is a cyclic alkyl group having a ring with three or more members, preferably a 3- to 6-membered cycloalkyl group. Examples of the cycloalkyl group include cyclopropyl group, cyclobutyl group, cyclopentyl group, cyclohexyl group, cycloheptyl group and the like.

The "alkylsulfonyl group" is a monovalent group in which —S(O)$_2$— is bonded to the terminal carbon atom of the alkyl group. The carbon number of the alkyl group of the alkylsulfonyl group is preferably 1 to 6. Examples of the alkylsulfonyl group include methanesulfonyl group, ethanesulfonyl group, propanesulfonyl group, butanesulfonyl group, pentanesulfonyl group, hexanesulfonyl group and the like.

The "arylsulfonyl group" is a monovalent group in which —S(O)$_2$— is bonded to the binding end of the aryl group. As the aryl group of the arylsulfonyl group, a group having 6-10 carbon atoms is preferable, and a group similar to the aforementioned aryl group is preferable. Examples of the arylsulfonyl group include an arylsulfonyl group having 6-10 carbon atoms such as benzenesulfonyl group, 1-naphthalenesulfonyl group, and 2-naphthalenesulfonyl group, and benzenesulfonyl group is preferable.

The "acyl group" is a monovalent group obtained by removing a hydroxy group from the carboxy group of carboxylic acid. As the carboxylic acid, carboxylic acid having 1-10 carbon atoms is preferable, formic acid, saturated aliphatic carboxylic acid (e.g., alkylcarboxylic acid such as acetic acid, propionic acid, and butyric acid), unsaturated aliphatic carboxylic acid (e.g., alkenylcarboxylic acid such as acrylic acid), carbocyclic carboxylic acid, heterocyclic carboxylic acid and the like can be mentioned.

Examples of the carbocyclic carboxylic acid include saturated cyclic aliphatic carboxylic acid (e.g., cycloalkylcarboxylic acid such as cyclopropylcarboxylic acid, cyclopentylcarboxylic acid, and cyclohexylcarboxylic acid), unsaturated cyclic aliphatic carboxylic acid (e.g., cycloalkenylcarboxylic acid such as cyclohexenylcarboxylic acid) and aromatic carboxylic acid. The aromatic carboxylic acid is a compound in which the aforementioned aryl group is bonded to a carboxy group and, for example, arylcarboxylic acid such as benzoic acid and naphthylcarboxylic acid can be mentioned. The heterocyclic carboxylic acid is a compound in which a heterocyclic group is bonded to the carboxy group.

The "heterocyclic group" is preferably a 3- to 10-membered monovalent saturated or unsaturated heterocyclic group containing at least one hetero atom selected from the group consisting of a nitrogen atom, an oxygen atom and a sulfur atom. Examples of the 3- to 10-membered saturated or unsaturated heterocycle include aziridine, azetidine, pyrrole, pyrroline, pyrrolidine, imidazole, imidazoline, imidazolidine, pyrazole, pyrazoline, pyrazolidine, pyridine, piperidine, pyrazine, piperazine, pyrimidine, pyridazine, thiazole, thiazoline, thiazolidine, isothiazole, isothiazoline, isothiazolidine, oxazole, oxazoline, oxazolidine, isoxazole, isoxazoline, isoxazolidine, morpholine, azepane, azepine and the like.

In the present specification, substitution of one or more hydrogen atoms in a group with a halogen atom is called halogenation. For example, a halogenated alkoxy group is a group in which one or more hydrogen atoms of an alkoxy group is/are substituted by a halogen atom. The same applies to other groups. As the halogen atom, a fluorine atom or a chlorine atom is preferable.

A preferable example of the halogenated group having a halogenated alkyl group in its structure is a halogenated lower alkyl group, and fluoromethyl group, difluoromethyl group, trifluoromethyl group, trifluoroethyl group, pentafluoroethyl group, chloromethyl group, bromomethyl group and the like can be mentioned.

The "alkoxyalkyl group" is an alkyl group in which one of the hydrogen atoms in the alkyl group is substituted by an alkoxy group. The alkoxy group in the alkoxyalkyl group is preferably an alkoxy group having 1 - 4 carbon atoms. The alkyl group in the alkoxyalkyl group is preferably an alkyl group having 1 - 4 carbon atoms. The carbon number of the alkoxyalkyl group is preferably 2 to 6, more preferably 2 to 4. Examples of the alkoxyalkyl group include methoxymethyl group, ethoxymethyl group, propoxymethyl group, ethoxyethyl group and the like.

The "hydroxyalkyl group" is a group in which one or more hydrogen atoms in the alkyl group is/are substituted by a hydroxy group. The carbon number of the hydroxyalkyl group is preferably 2 to 6. The number of hydroxy groups of the hydroxyalkyl group is preferably one. Examples of the hydroxyalkyl group include 2-hydroxyethyl group, 3-hydroxypropyl group, 2-hydroxypropyl group, 4-hydroxybutyl group and the like.

The "alkoxycarbonyl group" is a group in which the aforementioned alkoxy group is bonded the carbonyl group. The alkoxycarbonyl group is preferably an alkoxycarbonyl group in which an alkoxy group having 1-6 carbon atoms is bonded to a carbonyl group. Examples of the alkoxycarbonyl group include methoxycarbonyl group, ethoxycarbonyl group, n-propoxycarbonyl group, isopropoxycarbonyl group, n-butoxycarbonyl group, t-butoxycarbonyl group, amyloxycarbonyl group and the like.

The substituted alkyl group is a group in which one or more hydrogen atoms of the alkyl group is/are substituted by a substituent(s). Examples of the substituent include halogen atom, hydroxy group, alkoxy group, halogenated alkoxy group, acyl group, acyloxy group, halogenated acyloxy group, alkylsulfonyloxy group, halogenated alkylsulfonyloxy group, arylsulfonyloxy group, arylsulfonyloxy group substituted halogenated alkyl group, alkoxycarbonyloxy group, amino group, substituted amino group, aryl group, heterocyclic group and the like, with preference given to halogen atom, hydroxy group or alkoxy group.

The substituted cycloalkyl group is a group in which one or more hydrogen atoms in the cycloalkyl group is/are substituted by a substituent(s). Examples of the substituent include alkyl group, halogenated alkyl group, halogen atom, hydroxy group, alkoxy group, halogenated alkoxy group, acyloxy group, halogenated acyloxy group, alkylsulfonyloxy group, halogenated alkylsulfonyloxy group, arylsulfonyloxy group, halogenated arylsulfonyloxy group, arylsulfonyloxy group substituted by alkyl, alkoxycarbonyloxy group and the like, with preference given to alkyl group, halogen atom or alkoxy group.

Examples of the substituted cycloalkyl group include 2-methylcyclopropyl group, 2,2-dimethylcyclopropyl group, 2-fluorocyclopropyl group, 2-methylcyclobutyl group, 2,2-dimethylcyclobutyl group, 2-methylcyclopentyl group, 2-methylcyclohexyl group and the like.

The substituted aryl group is a group in which one or more hydrogen atoms of the aryl group is/are substituted by a substituent(s). The substituent of the substituted aryl group is halogen atom, alkyl group, halogenated alkyl group, hydroxy group, alkoxy group, halogenated alkoxy group, alkylenedioxy group having 1-3 carbon atoms (e.g., methylenedioxy group and ethylenedioxy group) or the like, with preference given to halogen atom, alkyl group, halogenated alkyl group, or alkoxy group.

Examples of the substituted aryl group include monohalophenyl group (e.g., 1-, 2- or 3-chlorophenyl group, 1-, 2- or 3-fluorophenyl group, and 1-, 2- or 3-bromophenyl group), (halogenated alkyl)phenyl group (e.g., 1-, 2- or 3-trifluoromethylphenyl group), and alkoxyphenyl group (e.g., 1-, 2- or 3-methoxyphenyl group and 1-, 2- or 3-ethoxyphenyl group).

The substituted alkylsulfonyl group is a group in which one or more hydrogen atoms of the alkylsulfonyl group is/are substituted by a substituent(s). As the substituent of the substituted alkylsulfonyl group, a halogen atom is preferable. Examples of the substituted alkylsulfonyl group include trifluoromethanesulfonyl group, pentafluoroethanesulfonyl group and the like.

The substituted arylsulfonyl group is a group in which one or more hydrogen atoms of the arylsulfonyl group is/are substituted by a substituent(s). The substituent of the substituted arylsulfonyl group is preferably halogen atom, alkyl group, halogenated alkyl group, or alkoxy group. Examples of the substituted arylsulfonyl group include monohalogenated phenylsulfonyl group (e.g., 1-, 2- or 3-chlorobenzenesulfonyl group, 1-, 2- or 3-fluorobenzenesulfonyl group, and 1-, 2- or 3-bromobenzenesulfonyl group), (alkyl)phenylsulfonyl group (e.g., p-toluenesulfonyl group), (halogenated alkyl)phenylsulfonyl group (e.g., trifluoromethylbenzenesulfonyl group) and (alkoxy)phenyl group (e.g., methoxybenzenesulfonyl group and ethoxybenzenesulfonyl group).

The substituted amino group is a group in which one or two hydrogen atoms of the amino group is/are substituted. When two hydrogen atoms of the amino group are substituted by substituents, the substituents may be the same or different. Examples of the substituent of the substituted amino group include the amino-protecting groups described in "Greene's/Protective/Groups/in/Organic/Synthesis 4th Edition" (P. G. M. Wuts, T. W. Greene, J. Wiley & Sons, 2007) and the like. Specifically, alkyl group having 1-6 carbon atoms, alkoxy group having 1-6 carbon atoms, alkenyl group having 2-6 carbon atoms, alkynyl group having 2-6 carbon atoms, aryl group having 6-10 carbon atoms, monovalent heterocyclic group, aralkyl group having 7-14 carbon atoms, benzhydryl group, trityl group, acyl group, tri-organosilyl group and the like can be mentioned. When the aforementioned substituent is a group containing a hydrogen atom, one or more of the hydrogen atoms may be further substituted by a substituent(s) (hereinafter to be indicated as substituent 2). As the substituent 2, halogen atom, alkyl group having 1-6 carbon atoms, alkoxy group having 1-6 carbon atoms, alkoxycarbonyl group having 1-6 carbon atoms, cyano group, nitro group and the like can be mentioned.

Examples of the substituent of the substituted amino group include methyl group, ethyl group, isopropyl group, benzyl group, phenyl group, pyridyl group, methoxy group, acetyl group, trifluoroacetyl group, pivaloyl group, benzoyl group, naphthoyl group, tert-butoxycarbonyl group, 2,2,2-trichloroethoxycarbonyl group, benzyloxycarbonyl group, 9-fluorenylmethyloxycarbonyl group, benzhydryl group, trityl group, phthaloyl group, allyloxycarbonyl group, methanesulfonyl group, trifluoromethanesulfonyl group, p-toluenesulfonyl group, o-nitrobenzenesulfonyl group, trimethylsilylethoxycarbonyl group, dimethylcarbamoyl group and the like.

In the compound of the present invention, when the substituent is a group selected from alkyl group, halogenated alkyl group, alkoxy group and halogenated alkoxy group, or a group having the selected group as a partial structure, the selected group is preferably a lower group.

In compound (1) of the present invention, $R^4$ in the α-chain is $-CH_2-CZ^1Z^2(COX)$ or $-CH=CZ^1(COX)$.

That is, compound (1) is a compound represented by the following formula (α1) or the following formula (α2).

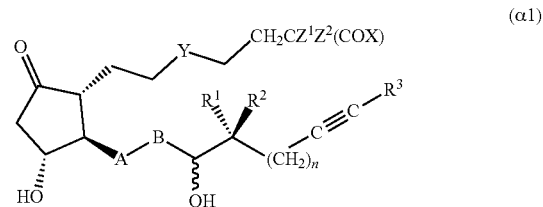

(α1)

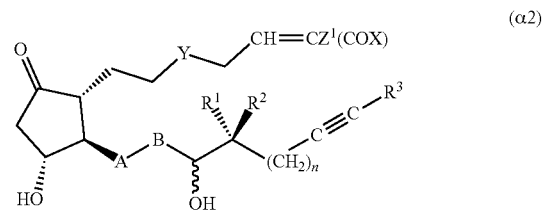

(α2)

Both $Z^1$ and $Z^2$ in compound (α1) are preferably hydrogen atoms or fluorine atoms.

The configuration of the group bonded to the double bond of the $CH=CZ^1(COX)$ moiety of compound (α2) may be E or Z. When $Z^1$ is a hydrogen atom, E is preferable, and when $Z^1$ is a fluorine atom, Z is preferable.

Furthermore, compound (α1) is preferably compound (α1-1) or compound (α1-2), and compound (α2) is preferably compound (α2-1) or (α2-2).

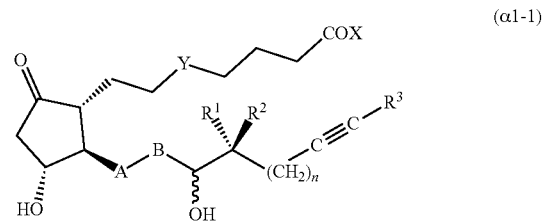

(α1-1)

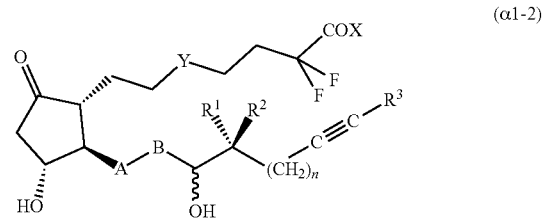

(α1-2)

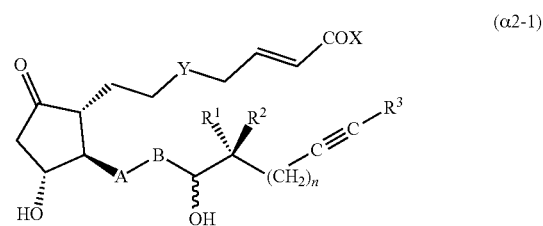

(α2-1)

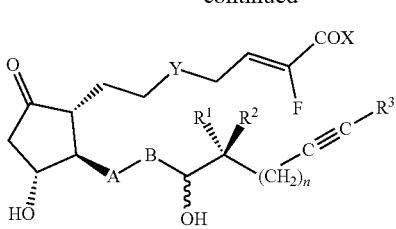

(α2-2)

In the aforementioned formulas, X is $OR^4$ or $NR^5R^6$, preferably $OR^4$. $R^4$ of $OR^4$ is preferably a hydrogen atom, an alkyl group having 1-4 carbon atoms or a substituted alkyl group having 1-4 carbon atoms. As the substituent, hydroxy group, acyl group, acyloxy group, alkoxycarbonyloxy group, substituted amine group, aryl group, heterocyclic group and the like can be mentioned, and acyl group and heterocyclic group are particularly preferable.

A compound in which X is $OR^4$ and $R^4$ is an alkyl group having 1-6 carbon atoms or a substituted alkyl group having 1-6 carbon atoms can also be led from a compound in which the COX moiety (i.e., $CO_2R^4$ moiety) has a structure that produces a prodrug of carboxylic acid.

Specific examples of $R^4$ include hydrogen atom, methyl group, ethyl group, n-propyl group, isopropyl group, n-butyl group, isobutyl group, sec-butyl group, tert-butyl group, benzyl group, pivaloylmethyl group, (5-methyl-2-oxo-1,3-dioxol-4-yl)methyl group, 2-hydroxyethyl group, 2-(dimethylamino)ethyl group, 2-(morpholino)ethyl group, 4-pyridylmethyl group, pivaloyloxymethyl group, 1-{[(1-cyclohexyloxy)carbonyl]oxy}ethyl group and the like. Preferred are hydrogen atom, alkyl group having 1-4 carbon atoms (e.g., methyl group and ethyl group), pivaloylmethyl group, and (5-methyl-2-oxo-1,3-dioxol-4-yl)methyl group, and particularly preferred are hydrogen atom, methyl group and ethyl group.

$R^5$ when X is $NR^5R^6$ is a hydrogen atom, an alkyl group having 1-6 carbon atoms or a substituted alkyl group having 1-6 carbon atoms. Examples of the alkyl group having 1-6 carbon atoms include methyl group, ethyl group, n-propyl group, isopropyl group, n-butyl group, isobutyl group, sec-butyl group, tert-butyl group and the like. $R^5$ is preferably a hydrogen atom, a methyl group, an ethyl group or the like.

$R^6$ is a hydrogen atom, an alkyl group having 1-6 carbon atoms, a substituted alkyl group having 1-6 carbon atoms, an alkylsulfonyl group having 1-6 carbon atoms, a substituted alkylsulfonyl group having 1-6 carbon atoms, an arylsulfonyl group having 6-10 carbon atoms or a substituted arylsulfonyl group having 6-10 carbon atoms.

When $R^6$ is an alkyl group having 1-6 carbon atoms or a substituted alkyl group having 1-6 carbon atoms, examples thereof include lower alkyl group such as methyl group, ethyl group, n-propyl group, isopropyl group, n-butyl group, isobutyl group, sec-butyl group, and tert-butyl group, hydroxyalkyl group such as 2-hydroxyethyl group, 3-hydroxypropyl group, 2-hydroxypropyl group, and 2,3-dihydroxypropyl group, and the like.

When $R^6$ is an alkylsulfonyl group having 1-6 carbon atoms or a substituted alkylsulfonyl group having 1-6 carbon atoms, examples thereof include methanesulfonyl group, ethanesulfonyl group and the like. Examples of the arylsulfonyl group having 6-10 carbon atoms or a substituted arylsulfonyl group having 6-10 carbon atoms include phenylsulfonyl group, p-toluenesulfonyl group and the like.

$R^6$ is preferably a hydrogen atom, a methyl group, an ethyl group, a hydroxyethyl group, a methanesulfonyl group, an ethanesulfonyl group or the like.

The structure of the moiety expressed by A-B shows that the A-B structure is a carbon-carbon single bond (i.e., —$CH_2$—$CH_2$—), a carbon-carbon double bond (i.e., —CH=CH—), or a carbon-carbon triple bond (i.e., —C≡C—). The structure of the A-B moiety is preferably a carbon-carbon single bond or a carbon-carbon double bond, and the configuration of the group bonded to the double bond is preferably E.

The hydroxy group bonded by a wavy line shows that the orientation of the bond of the hydroxy group is α-configuration (binding downward on the paper surface), β-configuration (binding upward on the paper surface) or a mixed configuration of α-configuration and β-configuration. The configuration of the hydroxy group is preferably α-configuration, or a mixed configuration of α-configuration and β-configuration, particularly preferably α-configuration.

Y is $CH_2$, S or O, preferably $CH_2$ or S, particularly preferably $CH_2$.

In the structure shown by $(CH_2)_n$, n is the number of methylene units. When n is 0, the methylene unit is absent. In this case, the carbon atom to which $R^1$ and $R^2$ are bonded, and the carbon atom of the triple bond are directly bonded to each other. n is preferably 1 or 2, particularly preferably 1.

$R^1$ and $R^2$ are each independently a hydrogen atom, an alkyl group having 1-3 carbon atoms or a substituted alkyl group having 1-3 carbon atoms. It is preferable that one of $R^1$ and $R^2$ is a hydrogen atom and the other is an alkyl group having 1-2 carbon atoms (preferably a methyl group), or $R^1$ and $R^2$ are alkyl groups having 1-2 carbon atoms (preferably a methyl group). It is more preferable that $R^1$ is a hydrogen atom and $R^2$ is an alkyl group having 1-2 carbon atoms, and particularly preferably, $R^1$ is a hydrogen atom and $R^2$ is a methyl group.

$R^3$ is an alkyl group having 1-4 carbon atoms, a substituted alkyl group having 1-4 carbon atoms, a cycloalkyl group having 3-6 carbon atoms, a substituted cycloalkyl group having 3-6 carbon atoms, an aryl group having 6-10 carbon atoms or a substituted aryl group having 6-10 carbon atoms. It is preferably an alkyl group having 1-4 carbon atoms or a cycloalkyl group having 3-6 carbon atoms, particularly preferably an alkyl group having 2-4 carbon atoms or a cycloalkyl group having 3-6 carbon atoms, further preferably an alkyl group having 2-3 carbon atoms or a cycloalkyl group having 3-5 carbon atoms, especially preferably a cycloalkyl group having 3-5 carbon atoms. Specific examples of $R^3$ include ethyl group, n-propyl group, isopropyl group, cyclopropyl group, cyclobutyl group, cyclopentyl group, phenyl group and the like. Ethyl group, cyclopropyl group or cyclobutyl group is preferable, and cyclopropyl group is particularly preferable.

In compound (1) of the present invention, a compound wherein ω-chain has the following structure is preferable.

[Compound (ω-1)]

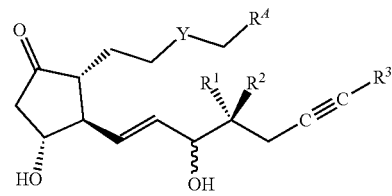

(ω-1)

The symbols in the formula (ω-1) have the same meanings as in the formula (1).

It is preferable that Y is CH$_2$ or S, R$^1$ is a hydrogen atom, R$^2$ is an alkyl group having 1-2 carbon atoms, R$^3$ is an alkyl group having 1-4 carbon atoms (preferably an alkyl group having 2-3 carbon atoms) or a cycloalkyl group having 3-6 carbon atoms (preferably a cycloalkyl group having 3-5 carbon atoms), X is OR$^4$, R$^4$ is a hydrogen atom, an alkyl group having 1-6 carbon atoms or a substituted alkyl group having 1-6 carbon atoms. Note that 7-((1R,2R,3R)-3-hydroxy-2-((1E,3S,4RS)-3-hydroxy-4-methyloct-1-en-6-yn-1-yl)-5-oxocyclopentyl)heptanoic acid is excluded from compound (ω-1). Furthermore, the substituent of the substituted alkyl group having 1-6 carbon atoms is preferably a group selected from hydroxy group, acyl group, acyloxy group, alkoxycarbonyloxy group, substituted amino group, aryl group and heterocyclic group.

As compound (1) of the present invention, a compound wherein the structure of α-chain and ω-chain is the following structure is preferable from the aspects of pharmacological activity and property.

[Compound (ω-10)]

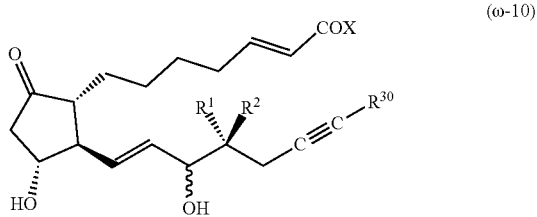

(ω-10)

The symbols in the formula (ω-10) have the same meanings as in the formula (1). R$^{30}$ is an alkyl group having 1-4 carbon atoms (preferably an alkyl group having 2-3 carbon atoms), or a cycloalkyl group having 3-6 carbon atoms (preferably a cycloalkyl group having 3-5 carbon atoms).

It is preferable that R$^1$ is a hydrogen atom, R$^2$ is an alkyl group having 1-2 carbon atoms, X is OR$^4$, and R$^4$ is a hydrogen atom or an alkyl group having 1-4 carbon atoms.

[Compound (ω-11)]

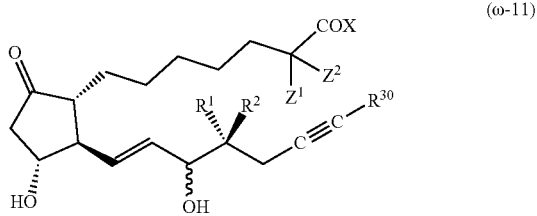

(ω-11)

The symbols in the formula (ω-11) have the same meanings as in the formula (1). R$^{30}$ is an alkyl group having 1-4 carbon atoms (preferably an alkyl group having 2-3 carbon atoms), or a cycloalkyl group having 3-6 carbon atoms (preferably a cycloalkyl group having 3-5 carbon atoms).

It is preferable that R$^1$ is a hydrogen atom, R$^2$ is an alkyl group having 1 - 2 carbon atoms, X is OR$^4$, and R$^4$ is a hydrogen atom or an alkyl group having 1 - 4 carbon atoms. Both Z$^1$ and Z$^2$ are preferably hydrogen atoms or fluorine atoms.

Preferable compounds (1) are shown below.
[Compound (1)-A]

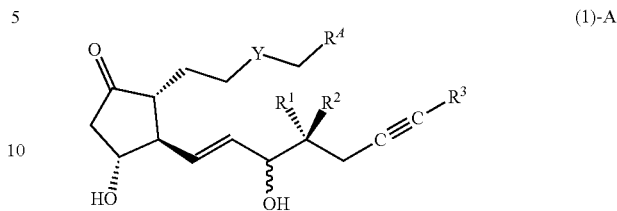

(1)-A

In the formula (1)-A, the configuration of a hydroxy group bonded by a wavy line is α-configuration, β-configuration, or a mixed configuration of α-configuration and β-configuration, Y is CH$_2$, S or O, R$^1$ is preferably a hydrogen atom, R$^2$ is preferably an alkyl group having 1-2 carbon atoms, R$^3$ is preferably an alkyl group having 1-4 carbon atoms or a cycloalkyl group having 3-6 carbon atoms, R$^4$ is —CH$_2$—CZ$^1$Z$^2$(COX) or —CH=CZ$^1$(COX), Z$^1$ and Z$^2$ are each independently a hydrogen atom or a fluorine atom, X is preferably OR$^4$, and R$^4$ is preferably a hydrogen atom, an alkyl group having 1-6 carbon atoms, or an alkyl group having 1-6 carbon atoms substituted by a substituent(s) selected from the group consisting of a hydroxy group, an acyl group, an acyloxy group, an alkoxycarbonyloxy group, a substituted amino group, an aryl group and a heterocyclic group. When R$^4$ is —CH=CZ$^1$(COX), the configuration of the group bonded to the double bond may be E or Z, when Z$^1$ is a hydrogen atom, E is preferable, and when Z$^1$ is a fluorine atom, Z is preferable. Note that 7-((1R,2R,3R)-3-hydroxy-2-((1E,3S,4RS)-3-hydroxy-4-methyloct-1-en-6-yn-1-yl)-5-oxocyclopentyl)heptanoic acid is excluded.

[Compound (1)-B]

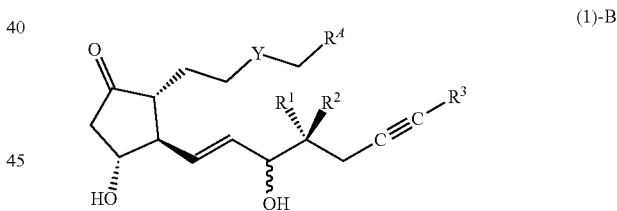

(1)-B

In the formula (1)-B, the configuration of a hydroxy group bonded by a wavy line is α-configuration, β-configuration, or a mixed configuration of α-configuration and β-configuration, Y is preferably CH$_2$ or S, R$^1$ is preferably a hydrogen atom, R$^2$ is preferably an alkyl group having 1-2 carbon atoms, R$^3$ is preferably an alkyl group having 2-3 carbon atoms or a cycloalkyl group having 3-5 carbon atoms, R$^4$ is —CH$_2$—CZ$^1$Z$^2$(COX) or —CH=CZ$^1$(COX), Z$^1$ and Z$^2$ are each independently a hydrogen atom or a fluorine atom, X is preferably OR$^4$, and R$^4$ is preferably a hydrogen atom, an alkyl group having 1-6 carbon atoms, or an alkyl group having 1-6 carbon atoms substituted by a substituent(s) selected from the group consisting of a hydroxy group, an acyl group, an acyloxy group, an alkoxycarbonyloxy group, a substituted amino group, an aryl group and a heterocyclic group. When R$^4$ is —CH=CZ$^1$(COX), the configuration of the group bonded to the double bond may be E or Z, when Z$^1$ is a hydrogen atom, E is preferable, and when Z$^1$ is a fluorine atom, Z is preferable.

[Compound (1)-C]

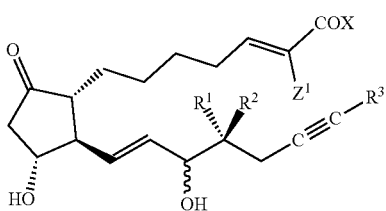

(1)-C

In the formula (1)-C, the configuration of a hydroxy group bonded by a wavy line is α-configuration, β-configuration, or a mixed configuration of α-configuration and β-configuration, $R^1$ is preferably a hydrogen atom, $R^2$ is preferably an alkyl group having 1-2 carbon atoms, $R^3$ is preferably an alkyl group having 2-3 carbon atoms, $Z^1$ is a hydrogen atom or a fluorine atom, X is preferably $OR^4$, and $R^4$ is preferably a hydrogen atom or an alkyl group having 1-4 carbon atoms.

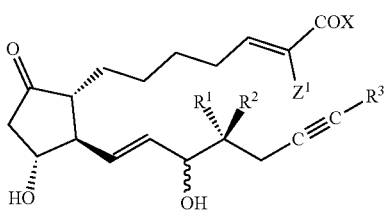

(1)-D

[Compound (1)-D]

In the formula (1)-D, the configuration of a hydroxy group bonded by a wavy line is α-configuration, β-configuration, or a mixed configuration of α-configuration and β-configuration, $R^1$ is preferably a hydrogen atom, $R^2$ is preferably an alkyl group having 1-2 carbon atoms, $R^3$ is preferably a cycloalkyl group having 3-5 carbon atoms, $Z^1$ is a hydrogen atom or a fluorine atom, X is preferably $OR^4$, and $R^4$ is preferably a hydrogen atom or an alkyl group having 1-4 carbon atoms.

[Compound (1)-E]

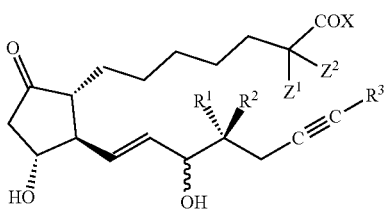

(1)-E

In the formula (1)-E, the configuration of a hydroxy group bonded by a wavy line is α-configuration, β-configuration, or a mixed configuration of α-configuration and β-configuration, $R^1$ is preferably a hydrogen atom, $R^2$ is preferably an alkyl group having 1-2 carbon atoms, $R^3$ is preferably an alkyl group having 2-3 carbon atoms, $Z^1$ and $Z^2$ are each independently a hydrogen atom or a fluorine atom, X is preferably $OR^4$, and $R^4$ is preferably a hydrogen atom or an alkyl group having 1-4 carbon atoms.

[Compound (1)-F]

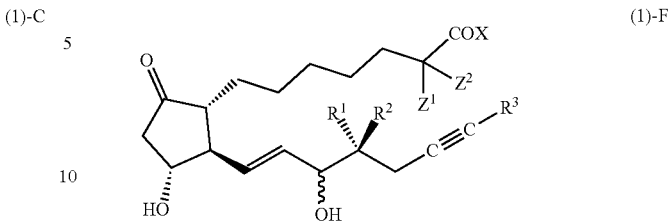

(1)-F

In the formula (1)-F, the configuration of a hydroxy group bonded by a wavy line is α-configuration, β-configuration, or a mixed configuration of α-configuration and β-configuration, $R^1$ is preferably a hydrogen atom, $R^2$ is preferably an alkyl group having 1-2 carbon atoms, $R^3$ is preferably a cycloalkyl group having 3-5 carbon atoms, $Z^1$ and $Z^2$ are each independently a hydrogen atom or a fluorine atom, X is preferably $OR^4$, and $R^4$ is preferably a hydrogen atom or an alkyl group having 1-4 carbon atoms.

Particularly preferable examples of compound (1) include the following compounds.

Methyl 4-((2-((1R,2R,3R)-3-hydroxy-2-((1E,3RS,4S)-3-hydroxy-4-methylnon-1-en-6-yn-1-yl)-5-oxocyclopentyl)ethyl)thio)butanoate [compound (1)-1], methyl (2E)-4-((2-((1R,2R,3R)-3-hydroxy-2-(1E,3RS,4S)-3-hydroxy-4-methylnon-1-en-6-yn-1-yl)-5-oxocyclopentyl)ethyl)thio)but-2-enoate [compound (1)-2], methyl ((1R,2R,3R)-3-hydroxy-2-((1E,3RS,4S)-3-hydroxy-4-methylnon-1-en-6-yn-1-yl)-5-oxocyclopentyl)heptanoate [compound (1)-3], (5-methyl-2-oxo-1,3-dioxol-4-yl)methyl 7-((1R,2R,3R)-3-hydroxy-2-((1E,3S,4S)-3-hydroxy-4-methylnon-1-en-6-yn-1-yl)-5-oxocyclopentyl)heptanoate [compound (1)-4], 3,3-dimethyl-2-oxobutyl 7-((1R,2R,3R)-3-hydroxy-2-((1E,3S,4S)-3-hydroxy-4-methylnon-1-en-6-yn-1-yl)-5-oxocyclopentyl)heptanoate [compound (1)-5], 7-((1R,2R,3R)-3-hydroxy-2-((1E,3S,4S)-3-hydroxy-4-methylnon-1-en-6-yn-1-yl)-5-oxocyclopentyl)heptanoic acid [compound (1)-6], (2E)-7-((1R,2R,3R)-3-hydroxy-2-((1E,3S,4S)-3-hydroxy-4-methylnon-1-en-6-yn-1-yl)-5-oxocyclopentyl)hept-2-enoic acid [compound (1)-7], 2,2-difluoro-7-((1R,2R,3R)-3-hydroxy-2-((1E,3S,4S)-3-hydroxy-4-methylnon-1-en-6-yn-1-yl)-5-oxocyclopentyl)heptanoic acid [compound (1)-8], 7-((1R,2R,3R)-2-((1E,3S,4S)-7-cyclopropyl-3-hydroxy-4-methylhept-1-en-6-yn-1-yl)-3-hydroxy-5-oxocyclopentyl) heptanoic acid [compound (1)-9], and (2E)-7-((1R,2R,3R)-2-((1E,3S,4S)-7-cyclopropyl-3-hydroxy-4-methylhept-1-en-6-yn-1-yl)-3-hydroxy-5-oxocyclopentyl)hept-2-enoic acid [compound (1)-10].

The compound of the present invention may be a pharmaceutically acceptable salt of compound (1). The salt is a salt of a carboxylic acid moiety with a basic substance (nontoxic inorganic base or nontoxic organic base), and has a structure in which the carboxylic acid moiety is —COO⁻ and the hydrogen atom of the carboxylic acid is a cation.

The pharmaceutically acceptable salt is, for example, a salt derived from a nontoxic inorganic base or a salt derived from a nontoxic organic base, and a salt derived from a nontoxic inorganic base is preferable.

Examples of the base derived from an inorganic salt include sodium salt, potassium salt, calcium salt, magnesium salt, zinc salt, aluminum salt, ammonium salt and the like, as well as lithium salt, copper salt, ferric salt, ferrous salt, manganese salt, manganous salt and the like, and sodium salt, potassium salt, calcium salt, magnesium salt and ammonium salt are preferable, and sodium salt and potassium salt are particularly preferable.

Examples of the salt derived from an organic base include salts with primary amine, secondary amine, tertiary amine, substituted amine of these (including naturally present substituted amine), cyclic amine, basic amino acid, basic ion exchange resin and the like. Examples of the organic amine and amino acid include isopropylamine, diethylamine, triethylamine, trimethylamine, tripropylamine, ethylenediamine, N,N'-dibenzylethylenediamine, 2-diethylaminoethanol, 2-dimethylaminoethanol, morpholine, N-ethylmorpholine, piperazine, piperidine, N-ethylpiperidine, betaine, caffeine, choline, glucamine, glucosamine, histidine, hydrabamine, methylglucamine, lysine, arginine, polyamine resin, procaine, purine, theobromine and the like.

Compound (1) or a pharmaceutically acceptable salt thereof may take the form of a hydrate or solvate.

Compound (1) of the present invention may be derived from a pharmaceutically acceptable prodrug of compound (1). The pharmaceutically acceptable prodrug is a compound having a group converted to a hydroxy group, a carboxy group or the like by solvolysis or under physiological conditions. Examples of the group forming a prodrug include the groups described in Prog. Med., 1985, vol. 5, pp. 2157-2161, and "IYAKUHIN no KAIHATSU (Development of Pharmaceuticals)", Vol. 7, Design of Molecules, pp. 163-198, Published by HIROKAWA SHOTEN (1990).

A prodrug of compound (1) is preferably a compound converted to a compound by a reaction due to an enzyme, gastric acid and the like in the body.

As the compound, the following compound (1-1)—compound (1-4) can be mentioned.

Compound (1-1) wherein the hydroxy group in compound (1) is acylated, alkylated, phosphorylated or borated.

Specifically, a compound wherein the hydroxy group in compound (1) is acetylated, propanoylated, butanoylated, pivaloylated, oleylated, palmitoylated, succinylated, fumarylated, alanylated, or dimethylaminomethylcarbonylated.

Compound (1-2) wherein the carboxy group in compound (1) is esterified or amidated. Specifically, a compound wherein the carboxy group in compound (1) is phenylesterified or phthalidyl-esterified, and the like.

Compound (1-3) wherein the carboxy group in compound (1) is substituted by a hydroxymethyl group.

Compound (1-4) wherein the carbonyl group of the 5-membered ring moiety in compound (1) is enol-esterified.

These compound (1-1)—compound (1-4) can be produced by a known method. Compound (1-1)—compound (1-4) may be a hydrate or a non-hydrate.

Compound (1) of the present invention or a pharmaceutically acceptable salt thereof may take the form of a clathrate compound of cyclodextrin. As the cyclodextrin, α-cyclodextrin, β-cyclodextrin, γ-cyclodextrin, sulfobutylether-β-cyclodextrin, hydroxypropyl-β-cyclodextrin, or a mixture of two or more kinds selected from these is used. As the cyclodextrin, α-cyclodextrin or β-cyclodextrin is preferable, and α-cyclodextrin is particularly preferable.

As the production method of a cyclodextrin clathrate compound, methods generally known widely as emulsion method, saturated aqueous solution method, kneading method, mixing and pulverizing method and the like can be used. Specifically, it can be produced using compound (1) or a pharmaceutically acceptable salt thereof, and cyclodextrin and by the method described in JP-B-50-3362, JP-B-2-31404 or JP-B-61-52146. By formulating compound (1) as a cyclodextrin clathrate compound, properties such as stability and water solubility increase, and properties preferable as pharmaceutical products can be imparted.

(Production Method of the Compound of the Present Invention)

The compound of the present invention can be synthesized by a general PG synthesis method. The concept of the synthetic route is shown in the following formulas.

For example, a compound wherein the -A-B— moiety is a double bond can be synthesized using a compound in which α-chain is introduced into Corey lactone as a starting material, by reducing the 15-position carbonyl group of the α,β-unsaturated carbonyl moiety in the ω-chain (compound of the following formula wherein W is H) introduced by a Horner-Wadsworth-Emmons reaction, introducing a double bond into the α-chain when desired, oxidizing the 9-position and deprotecting the hydroxy-protecting group.

A PG derivative having fluorine at the 2-position can be synthesized by, for example, synthesizing the starting material by introducing α-chain having a difluoro unit into Corey lactone, and performing a reaction similar to the above-mentioned reaction.

A compound wherein the -A-B— moiety is a single bond can be synthesized by performing 1,4-reduction of the α,β-unsaturated carbonyl moiety in the ω-chain (W in the following formula is H) introduced by a Horner-Wadsworth-Emmons reaction using Stryker's reagent ([(Ph$_3$P)CuH]$_6$), and a reducing agent such as sodium dithionite.

A compound wherein the -A-B— moiety is a triple bond can be synthesized by reducing, in the presence of a bromination agent such as N-bromosuccinimide and 1,3-dibromo-5,5-dimethylhydantoin, the 15-position carbonyl group of the α-bromo-α,β-unsaturated carbonyl moiety in the ω-chain (W in the following formula is a bromine atom) introduced by a Horner-Wadsworth-Emmons reaction, and performing a dehydrobromination reaction using sodium hydroxide, potassium tert-butoxide, or a base such as cesium acetate/18-crown-6.

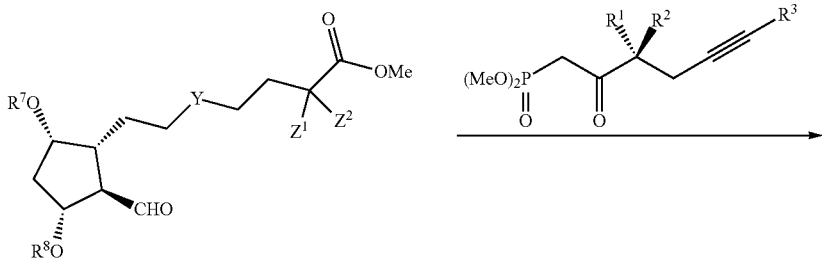

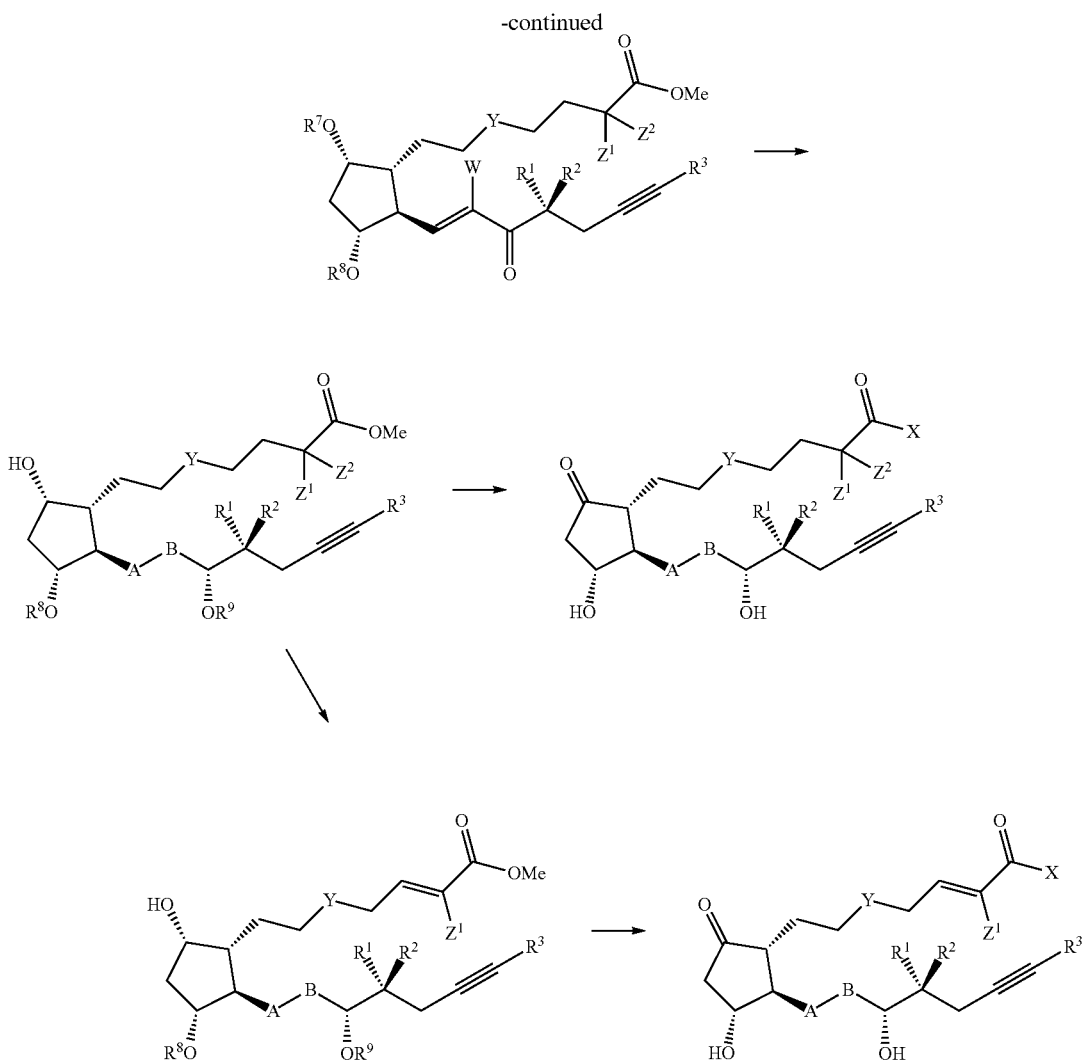

In the formulas, $R^7$, $R^8$ and $R^9$ are each independently a hydroxy-protecting group, W is a hydrogen atom or a bromine atom, and each of other symbols is as defined above.

As the hydroxy-protecting group for $R^7$-$R^9$, the hydroxy-protecting groups described in "Greene's/Protective/Groups/in/Organic/Synthesis 4th Edition" (by P. G. M. Wuts, T. W. Greene, J. Wiley & Sons, 2007), pp. 16-430 and the like can be used. Specifically, acyl group, tri-organosilyl group, alkoxyalkyl group, a monovalent group having a cyclic ether structure and the like can be mentioned. As the acyl group, acetyl group, benzoyl group, chloroacetyl group, dichloroacetyl group, trichloroacetyl group, trifluoroacetyl group and the like are preferable. As the tri-organosilyl group, a group in which three of alkyl group, aryl group, aralkyl group and alkoxy group are bonded to the silicon atom is preferable. Specifically, for example, tert-butyldimethylsilyl group, tert-butyldiphenylsilyl group, trimethylsilyl group, triethylsilyl group, triphenylsilyl group, triisopropylsilyl group and the like are preferable. As the alkoxyalkyl group, methoxymethyl group, benzyloxymethyl group, tert-butoxymethyl group, 2-methoxyethoxymethyl group, 1-ethoxyethyl group, 1-methyl-1-methoxyethyl group and the like are preferable. As the monovalent group having a cyclic ether structure, tetrahydropyranyl group, tetrahydrofuranyl group and the like are preferable. Acetyl group, benzoyl group, tetrahydropyranyl group, tert-butyldimethylsilyl group, tert-butyldiphenylsilyl group and the like are particularly preferable.

The hydroxy-protecting groups can be deprotected easily by a conventional method. Specifically, for example, they can be deprotected by the methods described in "Greene's/Protective/Groups/in/Organic/Synthesis 4th Edition" (by P. G. M. Wuts, T. W. Greene, J. Wiley & Sons, 2007), pp. 16-430 and the like.

A PG derivative in which the 5-position (Y) of the α-chain is a hetero atom can be synthesized as shown in the following by using Corey lactone that constructed ω-chain as a starting material, reducing the lactone moiety to give diol, introducing α-chain, oxidizing the 9-position, and deprotecting other hydroxy-protecting groups.

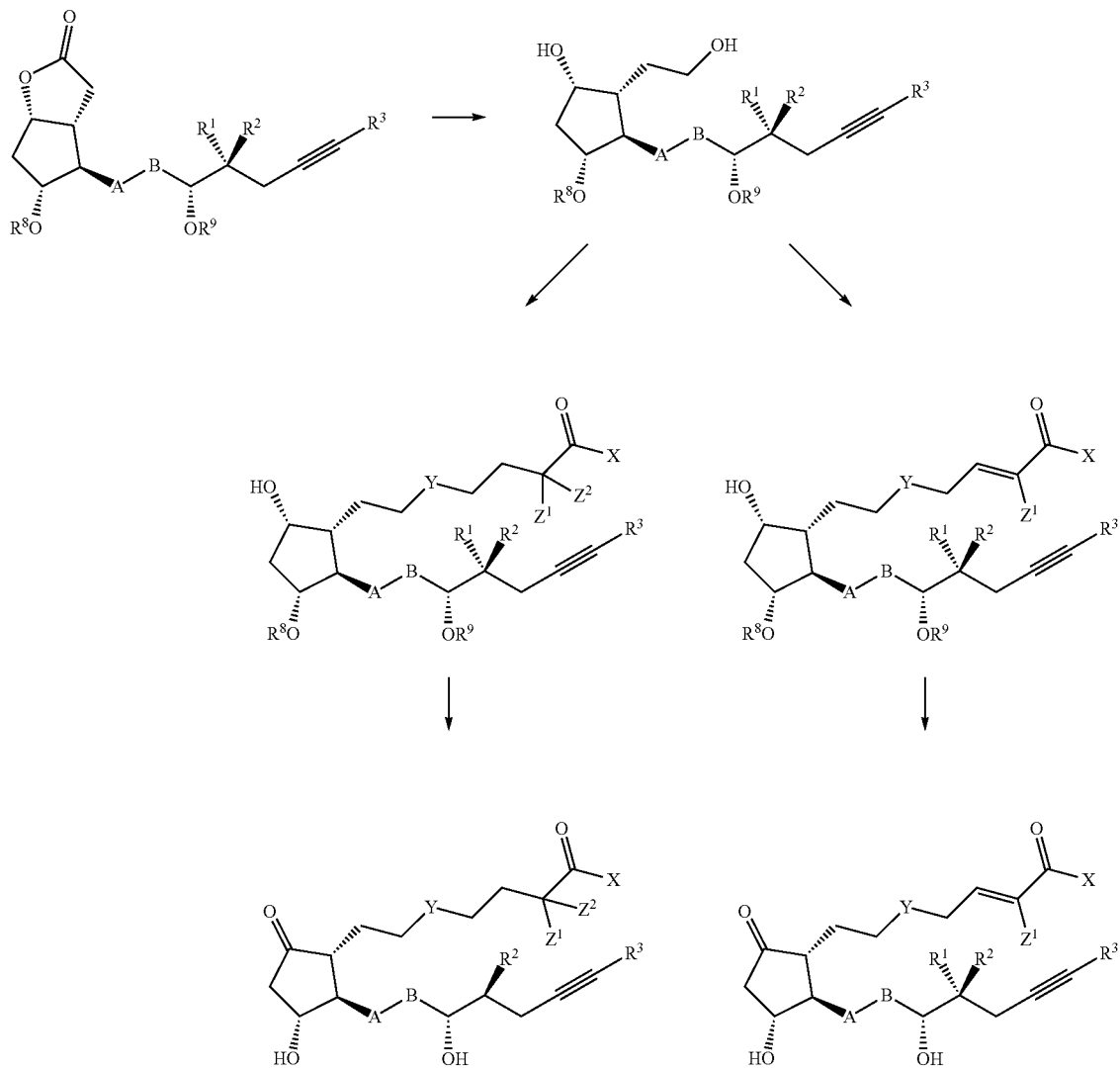
In the formulas, each symbol is as defined above.
Representative examples of the production method of compound (1) can be shown by the following formulas.
In the following formulas, the following abbreviations are used.
Me: methyl
Ac: acetyl
THP: tetrahydro-2H-pyran-2-yl
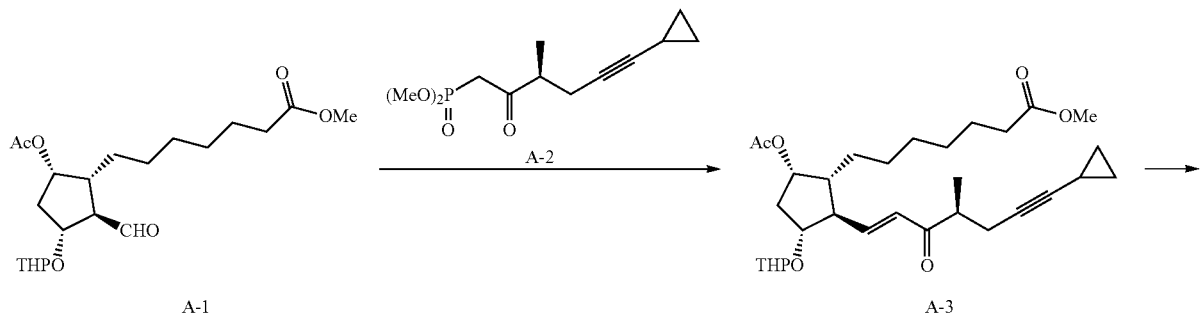

-continued

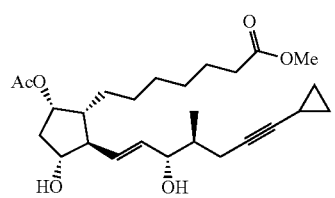

A-4

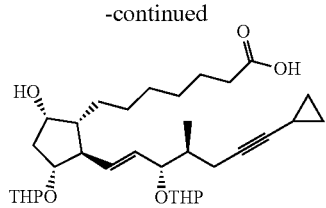

A-5

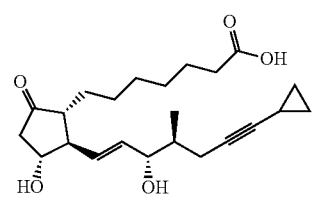

A-6

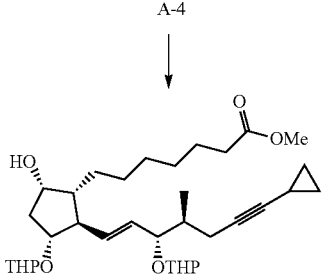

A-7

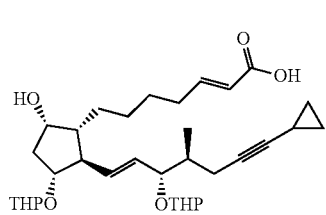

A-8

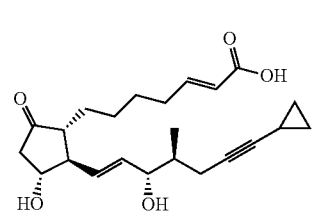

A-9

The starting material in the aforementioned formulas is aldehyde (A-1) described in JP-B-60-36422 and the like, and α,β-unsaturated ketone (A-3) is obtained from aldehyde (A-1) and phosphonate (A-2) by the Horner-Wadsworth-Emmons reaction. After reduction of the 15-position carbonyl group, deprotection is performed to give diol (A-4). After protection of the hydroxy group, hydrolysis is performed to give carboxylic acid (A-5). The unprotected hydroxy group on the 5-membered ring is oxidized and deprotected, whereby compound (A-6) of the present invention (compound (i)-9) can be synthesized.

After protection of two hydroxy groups of compound (A-4), deacetylation is performed to give alcohol (A-7). The α-position of the ester is phenylselenylated, an elimination reaction with hydrogen peroxide water is performed and ester hydrolysis is performed to give α,β-unsaturated carboxylic acid (A-8). The unprotected hydroxy group on the 5-membered ring is oxidized and deprotected, whereby compound (A-9) of the present invention (compound (1)-10) can be obtained.

For esterification of the carboxy group of compound (A-6) or (A-9) of the present invention, a general method, for example, the method described in "Shinjikken Kagaku Koza (Courses in Experimental Chemistry) 14 synthesis and reaction of organic compound (II)" (Maruzen Company, Limited) can be used. For example, methods such as esterification by condensation with alcohols and phenols, esterification by an O-alkylating agent, esterification using alkenes and alkynes, esterification by dialkyl sulfate and halogenated hydrocarbons and the like are used. For conversion to acylamides and sulfonamides, for example, the method of Tithereley et al. (J. Chem. Soc., 1904, vol. 85, p. 1673), the method of Lynch et al. (Can. J. Chem., 1972, vol. 50, p. 2143), the method of Davidson et al. (J. Am. Chem. Soc., 1958, vol. 80, p. 376) and the like can be adopted. In addition, a method including converting carboxylic acid to acid halide or active ester, then a condensation reaction directly with amides or sulfonamides, or a reaction with amines to once convert to amides, followed by acylation or sulfonylation and the like is used.

The compound of the present invention has an asymmetric carbon in the structure thereof. Thus, various stereoisomers and optical isomers are present. The present invention encompasses all stereoisomers, optical isomers, and mixtures thereof.

The compound of the present invention is a derivative less susceptible to metabolism in vivo and having improved stability. Compound (1) has an alkyl group at the 16-position carbon atom, and therefore, the hydroxy group at the 15-position of the PG skeleton is less susceptible to metabolism by PG dehydrogenase and shows high metabolic stability. Thus, it has a long half-life in blood and can maintain effective blood concentration for a long time as compared to natural type PG. Having improved metabolic stability, the compound can improve bioavailability of drugs.

The compound of the present invention has an alkynyl group in the ω-chain and shows very potent actions such as platelet aggregation suppressive activity. In particular, a derivative having a cycloalkyl group on the end of the alkynyl group is stable and exhibits potent activity.

The compound of the present invention and a cyclodextrin clathrate compound thereof are useful as medicaments, and can show a superior effect as a drug for circulatory diseases, central nervous system diseases, inflammatory diseases, pain and the like. Specifically, the circulatory diseases include peripheral circulation disorder, Buerger's disease, Raynaud's disease, angina pectoris, myocardial infarction, cardiac failure, pulmonary hypertension, pulmonary obliteration, diabetes, cerebral infarction, cerebral thrombus, deafness, Meniere's disease and the like. The central nervous system diseases include sleeplessness, anxiety, depression, schizophrenia, dementia and the like. The inflammatory diseases include acute hepatitis, chronic hepatitis, cirrhosis, cholecystitis, cholangitis, acute pancreatitis, chronic pancreatitis, chronic peritonitis, acute peritonitis, cystitis, acute nephritis, chronic nephritis, encephalitis, polyneuritis, meningitis, myelitis, arthritis, rheumatoid arthritis, bronchitis, pneumonia, pleurisy, phlebitis, pericarditis, rhinitis, pharyngitis, labyrinthitis, otitis externa and the like.

A medicament containing the compound of the present invention or a cyclodextrin clathrate compound thereof (hereinafter to be indicated as "the medicament of the present invention") is particularly useful as a medicament for the prophylaxis or treatment of blood flow disorders. The medicament of the present invention may be a medicament containing the compound of the present invention and optionally containing a pharmaceutically acceptable carrier and other therapeutic components.

When the medicament of the present invention is administered to patients as an agent for the prophylaxis or treatment of the aforementioned diseases, the daily dose varies depending on the age and body weight of patients, pathology and severity in patients, and the like. It is generally 0.00001 mg to 1 mg, preferably 0.0001 mg to 0.3 mg, as compound (1), which is desirably administered in one to several portions. For example, 0.0001 mg to 0.3 mg, particularly 0.001 mg to 0.1 mg, is preferable for oral administration. Meanwhile, 0.00001 mg to 0.1 mg, particularly 0.0001 mg to 0.03 mg, is preferable for intravenous administration. The dose can be appropriately increased or decreased according to the disease or pathology, and continuous drip administration is sometimes desirable in the case of injection.

The medicament of the present invention can be administered to the body by oral administration or parenteral administration (e.g., blood vessel (intravenous and intraarterial) administration, intrarectal administration, and intraarticular administration). Examples of the administration form include oral administration forms such as tablet (including orally disintegrating tablet and sublingual tablet), film (including oral films), capsule (including soft capsule and microcapsule), granule, powder, troche, and syrup, and parenteral administration forms such as liquid injection such as solution, emulsion, and suspension (e.g., subcutaneous injection, intravenous injection, intramuscular injection, intraperitoneal injection, and drip infusion), suppository (e.g., rectal suppository and vaginal suppository), eye drop, nasal drop, external preparation (e.g., transdermal preparation such as adhesive preparation, ointment, and cream), and pulmonary preparation (inhalant etc.). These preparations may be controlled-release preparations such as rapid release preparation and sustained-release preparation.

The preparation in the aforementioned administration form can be produced by adding additives necessary for preparations such as general carrier, excipient, lubricant, disintegrant, binder, and stabilizer to the medicament of the present invention and formulating the resulting mixture by a conventional method. For example, when the preparation is a tablet, granule, powder or the like, it can be produced using any pharmaceutical carriers suitable for producing a solid preparation, for example, excipient, lubricant, disintegrant, and binder.

Examples of the excipient include lactose, glucose, fructose, maltose, isomerized lactose, reduced lactose, lactose crystal, saccharose, D-mannitol, erythritol, maltitol, xylitol, palatinose, trehalose, sorbitol, cornstarch, potato starch, wheat starch, rice starch, crystalline cellulose, dextrans (e.g., dextran, dextran 40, and dextran 70), pullulan, dextrin, talc, silicic anhydride, anhydrous calcium phosphate, precipitated calcium carbonate, calcium silicate and the like.

Examples of the lubricant include magnesium stearate, calcium stearate, sucrose fatty acid ester, sodium stearyl fumarate, stearic acid, talc, polyethylene glycol, beeswax and the like.

Examples of the disintegrant include starch, carboxymethylcellulose, hydroxypropylcellulose, carmellose, carmellose calcium, sodium carboxymethyl starch, croscarmellose sodium, hydroxypropylstarch and the like.

Examples of the binder include crystalline cellulose, hydroxypropylcellulose, hydroxypropylmethylcellulose, hydroxyethylcellulose, methylcellulose, sodium carboxymethylcellulose, partially pregelatinized starch, pregelatinized starch, sodium alginate, pullulan, gum arabic, dextrin, polyvinylpyrrolidone, poly(vinyl alcohol), gelatin and the like.

A preparation in the aforementioned administration form may contain inert diluent, lubricant, stabilizer, solubilizing agent, corrigent and the like as necessary. Examples of the inert diluent include calcium carbonate, sodium carbonate, lactose, calcium phosphate, sodium phosphate and the like. Examples of the lubricant include magnesium stearate, stearic acid, colloidal silica, talc and the like. Examples of the stabilizer include ascorbic acid, sodium sulfite, glycine, L-aspartic acid, tocopheryl acetate, β-cyclodextrin, fumaric acid and the like. Examples of the solubilizing agent include polyethylene glycol, propylene glycol, glutamic acid, aspartic acid and the like. Examples of the corrigent include citric acid, ascorbic acid, lactic acid, acetic acid, tartaric acid, malic acid, aspartame, acesulfame potassium, thaumatin, saccharin sodium, dipotassium glycyrrhetinate, sodium glutamate, sodium 5'-inosinate, sodium 5'-guanylate and the like.

These tablets may be uncoated, or coated by a known technique to delay disintegration and absorption in the gastrointestinal tract, thereby ensuring a sustained action for a longer time. For example, a time delay material, for example, glyceryl monostearate or glyceryl distearate may be used.

The medicament of the present invention may be provided as a hard gelatin capsule containing a mixture with an inert solid diluent, for example, calcium carbonate, sodium carbonate, lactose, calcium phosphate, sodium phosphate or kaolin. In addition, the medicament of the present invention may be provided as a soft gelatin capsule containing a mixture with water-miscible solvent, for example, alcohols such as propylene glycol, polyethylene glycol, glycerol, and ethanol and an oil medium.

Examples of the oil medium include fatty acid ester, liquid paraffin, vegetable oil such as peanut oil and olive oil and the like. Fatty acid ester is a compound in which a carboxy group of fatty acid forms an ester bond with alcohol and, specifically, glyceride optionally having a saturated or unsaturated branched chain, fatty acid ester composed of an ester compound of fatty acid and monohydric alcohol and the like can be mentioned. Preferable fatty acid is medium-chain or long-chain fatty acid having 6-24 carbon atoms, and caproic acid, caprylic acid, capric acid, lauric acid, myristic acid, palmitic acid, palmitoleic acid, stearic acid, oleic acid, linoleic acid, linolenic acid, ricinoleic acid, arachidonic acid and the like can be mentioned. Preferable alcohols include monohydric alcohols having 1-6 carbon atoms, polyols which are polyhydric alcohols such as glycerol, polyethylene glycol, and propylene glycol and the like. Preferable fatty acid esters include glyceride optionally having saturated or unsaturated branch, glycerol fatty acid ester, and propyleneglycol fatty acid ester. In addition, a mixture of two or more kinds of glycerides can also be used. The mixtures of glycerides include a mixture of caprylic acid triglyceride and capric acid triglyceride, vegetable oil such as castor oil, corn oil, olive oil, sesame oil, rape seed oil, salad oil, cottonseed oil, camellia oil, peanut oil, palm oil, and sunflower oil. Examples of the fatty acid ester composed of an ester compound of fatty acid and monohydric alcohol include isopropyl myristate, isopropyl palmitate, ethyl linoleate, ethyl oleate and the like.

The major component of the coating film of the capsule is not particularly limited and, for example, various known components such as gelatin, carrageenan, pectin, pullulan, sodium alginate, starch, hypromellose, and hydroxypropylcellulose can be mentioned.

Preferable examples of the plasticizer used for the production of the coating film of soft capsules include polyhydric alcohol such as glycerol, ethylene glycol, polyethylene glycol, propylene glycol, and polypropylene glycol, sugar alcohol such as sorbitol, mannitol, xylitol, maltitol, cornstarch-derived sugar alcohol solution, and reduced maltose syrup, and the like. Two or more kinds of these plasticizers may be used in combination.

When the preparation is liquid such as syrup, solution, emulsion, and suspension, for example, it can be produced by appropriately selecting stabilizer, suspending agent, corrigent, aromatic, soothing agent and the like. When injection is produced, it can be aseptically prepared by dissolving the active ingredient together with a pH adjuster such as hydrochloric acid, sodium hydroxide, sodium lactate, acetic acid, sodium hydrogen phosphate, and sodium dihydrogen phosphate; an isotonicity agent such as sodium chloride, glucose, D-sorbitol, glycerol, and D-mannitol; a surfactant such as stearylethanolamine, sodium lauryl sulfate, lauryl aminopropionate, lecithin, benzalkonium chloride, and glycerol monostearate; a suspending agent such as poly(vinyl alcohol), polyvinylpyrrolidone, sodium carboxymethylcellulose, methylcellulose, hydroxymethylcellulose, hydroxyethylcellulose, and hydroxypropylcellulose; and a soothing agent such as benzyl alcohol in distilled water for injection. It may also be prepared using an inert non-aqueous diluent such as propylene glycol, polyethylene glycol, olive oil, ethanol, and polysorbate 80. Furthermore, injection to be dissolved when in use may be prepared by adding mannitol, dextrin, cyclodextrin, gelatin and the like and freeze-drying the resulting mixture in vacuum. For stabilization and improving lesion reachability, a liposome preparation may also be prepared by a known method and used as an injection. What is called a lipid preparation (fat emulsion) in which the compound of the present invention is dissolved in fine fat emulsion particles can also be prepared, and it can be produced by mixing an oil component such as fatty acid glycerides; phospholipid such as egg-yolk lecithin and soybean lecithin; and additives such as emulsion adjuvant, stabilizer, polymer substance, and isotonicity agent as necessary.

In addition, an intrarectal administration preparation may be prepared by using a base for suppository such as cacao butter, fatty acid triglyceride, fatty acid diglyceride, fatty acid monoglyceride, and polyethylene glycol. Furthermore, an intrarectally injecting ointment can also be prepared by adjusting to a suitable viscosity with a water-soluble base such as polyethylene glycol, polypropylene glycol, glycerol, and glycerolgelatin, an oily base such as white petrolatum, hard fat, paraffin, liquid paraffin, plastibase, lanolin, and purified lanolin, and the like.

The medicament of the present invention can be administered topically to the skin or mucosa, i.e., transdermally or transmucosally. Examples of the general dosage form for this object include gel, hydrogel, lotion, solution, cream, ointment, dusting powder, dressing agent, foam preparation, film, skin patch, wafer, implant, sponge, fiber, bandage, microemulsion and the like. Examples of the general carrier include alcohol, water, mineral oil, liquid paraffin, white petrolatum, glycerol, polyethylene glycol, propylene glycol and the like.

The medicament can be directly administered to the eye or ear, in the form of an isotonic, pH controlled eye drop of a suspension of fine powder or solution in sterile saline. Other dosage forms suitable for ocular or aural administration include ointment, biodegradable implant, non-biodegradable implant, wafer, lens, microparticles such as liposome, and the like. Crosslinked polyacrylic acid, poly(vinyl alcohol), hyaluronic acid, cellulose polymers such as hydroxypropylmethyl cellulose, hydroxyethyl cellulose, and methyl cellulose, or polymers such as complex polysaccharides such as gellan gum can be mixed with a preservative such as benzalkonium chloride.

To produce a pulmonary administration preparation, the medicament of the present invention is dissolved or dispersed in a conventional spray and filled in a pressure resistant container. It can also be pulmonarily administered as a liposome preparation by a known method.

In order to use the medicament of the present invention in any of the aforementioned administration forms and improve solubility, dissolution rate, bioavailability and/or stability thereof, the medicament can be further mixed with cyclodextrin and an appropriate derivative thereof or a soluble polymer unit of polyethylene glycol-containing polymer and the like. For example, a mixture, a complex etc. of these have been confirmed to be generally useful for most dosage forms and administration routes. Both inclusion and non-inclusion complexes can be used. As an alternative method for directly forming a complex with a drug, cyclodextrin can also be used as an auxiliary additive, i.e., carrier, excipient or solubilizer. For these objects, α-cyclodextrin, β-cyclodextrin, hydroxypropyl-β-cyclodextrin, γ-cyclodextrin and the like are generally used.

The compound of the present invention may be a pharmaceutically acceptable salt of a compound represented by the formula (1). As the salt, those mentioned above can be recited.

s Other therapeutic components (hereinafter to be also referred simply to as "other drugs") to be contained in the medicament of the present invention are not particularly limited as long as they are drugs that supplement and/or enhance the prophylactic and/or therapeutic effect of the compound of the present invention on blood flow disorders (e.g., spinal canal stenosis) and the like, drugs that can improve pharmacokinetics and absorption of the compound of the present invention and reduce the dose of the compound of the present invention, drugs that reduce the side effects of the compound of the present invention and the like.

Examples of other drugs for supplementing and/or enhancing the prophylactic and/or therapeutic effect of the compound of the present invention on blood flow disorders (e.g., spinal canal stenosis) and the like include, but are not limited to, prostaglandins, prostaglandin derivative preparations, vasodilators, anti-platelet drugs (platelet aggregation inhibitors), analgesic drugs, vitamins, muscle relaxants, antidepressants and the like.

Examples of the prostaglandins include PG receptor agonist, PG receptor antagonist and the like. Examples of the PG receptor include PGE receptor (EP1, EP2, EP3, and EP4), PGD receptor (DP and CRTH2), PGF receptor (FP), PGI receptor (IP), TX receptor (TP) and the like. Examples of the prostaglandin derivative preparation include limaprost, beraprost and the like.

Examples of the vasodilator include angiotensin converting enzyme inhibitor (e.g., captopril, enalapril, and delapril), angiotensin II antagonist (e.g., candesartan cilexetil, losartan, eprosartan, valsartan, telmisartan, irbesartan, olmesartan medoxomil, tasosartan, 1-{[2'-(2,5-dihydro-5-oxo-4H-1,2,4-oxadiazol-3-yl)biphenyl-4-yl]methyl}-2-ethoxy-1H-benzimidazole-7-carboxylic acid), calcium channel blocker (e.g., manidipine, nifedipine, nicardipine, amlodipine, and efonidipine), potassium channel opener (e.g., levcromakalim, L-27152, AL0671, and NIP-121), clonidine and the like.

Examples of the anti-platelet drug (platelet aggregation inhibitor) include clopidogrel sulfate, ticlopidine hydrochloride, cilostazol, ethyl icosapentate, sarpogrelate hydrochloride and the like.

Examples of the analgesic drug include acetaminophen, non-steroidal antiinflammatory drugs, neuropathic pain relieving drugs, pyrazolone drugs and the like. For example, sodium salicylate, aspirin, aspirin-dialuminate formulation, diflunisal, indomethacin, suprofen, ufenamate, dimethylisopropylazulene, bufexamac, felbinac, diclofenac, tolmetin sodium, clinoril, fenbufen, nabumetone, proglumetacin, indomethacin farnesyl, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranoprofen, loxoprofen sodium, alminoprofen, zaltoprofen, mefenamic acid, mefenamic acid aluminum, tolfenamic acid, floctafenine, ketophenylbutazone, oxyphenbutazone, piroxicam, tenoxicam, ampiroxicam, epirizole, tiaramide hydrochloride, tinoridine hydrochloride, emorfazone, neurotropin, pregabalin, sulpyrine, migrenin, pyrine cold remedies, dimetotiazine mesylate, simetride combination drug, non-pyrine cold remedies and the like can be mentioned.

Examples of the vitamin include mecobalamin and the like.

Examples of the muscle relaxant include tolperisone hydrochloride, chlorzoxazone, chlormezanone, methocarbamol, phenprobamate, pridinol mesylate, chlorphenesin, baclofen carbamate, eperisone hydrochloride, afloqualone, tizanidine hydrochloride, alcuronium chloride, suxamethonium chloride, tubocurarine chloride, dantrolene sodium, pancuronium bromide, vecuronium bromide and the like.

Examples of the antidepressant include tricyclic or tetracyclic antidepressant, SSRI (selective serotonin reuptake inhibitor), SNRI (serotonin-noradrenaline reuptake inhibitor) and the like. Examples of the tricyclic antidepressant include imipramine hydrochloride, desipramine hydrochloride, clomipramine hydrochloride, trimipramine maleate, amitriptyline hydrochloride, nortriptyline hydrochloride, lofepramine hydrochloride, amoxapine, dosulepin hydrochloride and the like, and examples of the tetracyclic antidepressant include maprotiline, mianserin and the like. Examples of SSRI include paroxetine hydrochloride hydrate and the like, and examples of SNRI include milnacipran hydrochloride, duloxetine hydrochloride and the like.

The weight ratio of the compound of the present invention to other drugs is not particularly limited, and any two or more kinds of other drugs may be administered in combination.

Preferable embodiments of the present invention are the following inventions.

<1> Compound (1) or a pharmaceutically acceptable salt thereof;
<2> the compound or a pharmaceutically acceptable salt thereof of the above-mentioned <1>, wherein Y is $CH_2$ or S;
<3> the compound or a pharmaceutically acceptable salt thereof of the above-mentioned <2>, wherein Y is $CH_2$;
<4> the compound or a pharmaceutically acceptable salt thereof of any of the above-mentioned <1>-<3>, wherein $R^A$ is —CH=$CZ^1$(COX);
<5> the compound or a pharmaceutically acceptable salt thereof of any of the above-mentioned <1>-<3>, wherein $R^A$ is —$CH_2$—$CZ^1Z^2$(COX);
<6> the compound or a pharmaceutically acceptable salt thereof of any of the above-mentioned <1>-<5>, wherein n is 1;
<7> the compound or a pharmaceutically acceptable salt thereof of any of the above-mentioned <1>-<6>, wherein A-B is a carbon-carbon double bond;
<8> the compound or a pharmaceutically acceptable salt thereof of any of the above-mentioned <1>-<7>, wherein $Z^1$ and $Z^2$ are hydrogen atoms;
<9> the compound or a pharmaceutically acceptable salt thereof of any of the above-mentioned <1>-<8>, wherein $R^1$ is a hydrogen atom and $R^2$ is an alkyl group having 1-3 carbon atoms;
<10> the compound or a pharmaceutically acceptable salt thereof of the above-mentioned <9>, wherein $R^2$ is a methyl group;
<11> the compound or a pharmaceutically acceptable salt thereof of any of the above-mentioned <1>-<10>, wherein $R^3$ is an alkyl group having 1-4 carbon atoms or a cycloalkyl group having 3-6 carbon atoms;
<12> the compound or a pharmaceutically acceptable salt thereof of the above-mentioned <11>, wherein $R^3$ is an alkyl group having 2-4 carbon atoms or a cycloalkyl group having 3-6 carbon atoms;
<13> the compound or a pharmaceutically acceptable salt thereof of the above-mentioned <12>, wherein $R^3$ is a cycloalkyl group having 3-6 carbon atoms;
<14> the compound or a pharmaceutically acceptable salt thereof of the above-mentioned <12>, wherein $R^3$ is an alkyl group having 2-3 carbon atoms or a cycloalkyl group having 3-5 carbon atoms;
<15> the compound or a pharmaceutically acceptable salt thereof of the above-mentioned <14>, wherein $R^3$ is a cycloalkyl group having 3-5 carbon atoms;
<16> the compound or a pharmaceutically acceptable salt thereof of any of the above-mentioned <1>-<15>, wherein X is $OR^4$;
<17> the compound or a pharmaceutically acceptable salt thereof of the above-mentioned <16>, wherein $R^4$ is a hydrogen atom, an alkyl group having 1-6 carbon atoms or a substituted alkyl group having 1-6 carbon atoms;
<18> the compound or a pharmaceutically acceptable salt thereof of the above-mentioned <17>, wherein $R^4$ is a hydrogen atom, an alkyl group having 1-6 carbon atoms, or an alkyl group having 1-6 carbon atoms substituted by a substituent(s) selected from the group consisting of a hydroxy group, an acyl group, an acyloxy group, an alkoxycarbonyloxy group, a substituted amino group, an aryl group and a heterocyclic group;
<19> the compound or a pharmaceutically acceptable salt thereof of the above-mentioned <17>, wherein $R^4$ is a hydrogen atom, an alkyl group having 1-4 carbon atoms or a substituted alkyl group having 1-4 carbon atoms;
<20> the compound or a pharmaceutically acceptable salt thereof of the above-mentioned <19>, wherein $R^4$ is a hydrogen atom, an alkyl group having 1-4 carbon atoms, or an alkyl group having 1-4 carbon atoms substituted by a substituent(s) selected from the group consisting of a hydroxy group, an acyl group, an acyloxy group, an alkoxycarbonyloxy group, a substituted amino group, an aryl group and a heterocyclic group;
<21> the compound or a pharmaceutically acceptable salt thereof of the above-mentioned <20>, wherein $R^4$ is a hydrogen atom, an alkyl group having 1-4 carbon atoms, a pivaloylmethyl group or a (5-methyl-2-oxo-1,3-dioxol-4-yl) methyl group;
<22> a cyclodextrin clathrate compound or a pharmaceutically acceptable salt thereof of the compound of any of the above-mentioned <1>-<21>;

<23> a medicament comprising the compound or a pharmaceutically acceptable salt thereof of any of the above-mentioned <1>-<21>, or the cyclodextrin clathrate compound of the above-mentioned <22> as an active ingredient;
<24> the medicament of the above-mentioned <23>, which is a prophylactic or therapeutic agent for a blood flow disorder;
<25> the medicament of the above-mentioned <24>, wherein the blood flow disorder is a blood flow disorder of nerve;
<26> the medicament of the above-mentioned <25>, wherein the blood flow disorder of nerve is a blood flow disorder associated with spinal canal stenosis;
<27> the medicament of the above-mentioned <24>, wherein the blood flow disorder is a blood flow disorder of peripheral artery, skin or brain;
<28> the medicament of the above-mentioned <27>, wherein the blood flow disorder of peripheral artery is a blood flow disorder associated with chronic arterial occlusion or pulmonary hypertension;
<29> the medicament of the above-mentioned <27>, wherein the blood flow disorder of skin is a blood flow disorder associated with pressure ulcer;
<30> the medicament of the above-mentioned <27>, wherein the blood flow disorder of brain is a blood flow disorder associated with suppression of recurrence after cerebral infarction;
<31> the compound or a pharmaceutically acceptable salt thereof of any of the above-mentioned <1>-<21>, or the cyclodextrin clathrate compound of the above-mentioned <22> for use in the prophylaxis or treatment of a blood flow disorder;
<32> the compound or a pharmaceutically acceptable salt thereof, or the cyclodextrin clathrate compound for use of the above-mentioned <31>, wherein the blood flow disorder is a blood flow disorder of nerve;
<33> the compound or a pharmaceutically acceptable salt thereof, or the cyclodextrin clathrate compound for use of the above-mentioned <32>, wherein the blood flow disorder of nerve is a blood flow disorder associated with spinal canal stenosis;
<34> the compound or a pharmaceutically acceptable salt thereof, or the cyclodextrin clathrate compound for use of the above-mentioned <31>, wherein the blood flow disorder is a blood flow disorder of peripheral artery, skin or brain;
<35> the compound or a pharmaceutically acceptable salt thereof, or the cyclodextrin clathrate compound for use of the above-mentioned <34>, wherein the blood flow disorder of peripheral artery is a blood flow disorder associated with chronic arterial occlusion or pulmonary hypertension;
<36> the compound or a pharmaceutically acceptable salt thereof, or the cyclodextrin clathrate compound for use of the above-mentioned <34>, wherein the blood flow disorder of skin is a blood flow disorder associated with pressure ulcer;
<37> the compound or a pharmaceutically acceptable salt thereof, or the cyclodextrin clathrate compound for use of the above-mentioned <34>, wherein the blood flow disorder of brain is a blood flow disorder associated with suppression of recurrence after cerebral infarction;
<38> a method for prophylaxis or treatment of a blood flow disorder in a mammal, comprising administering an effective amount of the compound or a pharmaceutically acceptable salt thereof of any of the above-mentioned <1>-<21>, or the cyclodextrin clathrate compound of the above-mentioned <22> to the mammal;
<39> the method of the above-mentioned <38>, wherein the blood flow disorder is a blood flow disorder of nerve;
<40> the method of the above-mentioned <39>, wherein the blood flow disorder of nerve is a blood flow disorder associated with spinal canal stenosis;
<41> the method of the above-mentioned <38>, wherein the blood flow disorder is a blood flow disorder of peripheral artery, skin or brain;
<42> the method of the above-mentioned <41>, wherein the blood flow disorder of peripheral artery is a blood flow disorder associated with chronic arterial occlusion or pulmonary hypertension;
<43> the method of the above-mentioned <41>, wherein the blood flow disorder of skin is a blood flow disorder associated with pressure ulcer;
<44> the method of the above-mentioned <41>, wherein the blood flow disorder of brain is a blood flow disorder associated with suppression of recurrence after cerebral infarction;
<45> use of the compound or a pharmaceutically acceptable salt thereof of any of the above-mentioned <1>-<21>, or the cyclodextrin clathrate compound of the above-mentioned <22> in the manufacture of a prophylactic or therapeutic agent for a blood flow disorder;
<46> the use of the above-mentioned <45>, wherein the blood flow disorder is a blood flow disorder of nerve;
<47> the use of the above-mentioned <46>, wherein the blood flow disorder of nerve is a blood flow disorder associated with spinal canal stenosis;
<48> the use of the above-mentioned <45>, wherein the blood flow disorder is a blood flow disorder of peripheral artery, skin or brain;
<49> the use of the above-mentioned <48>, wherein the blood flow disorder of peripheral artery is a blood flow disorder associated with chronic arterial occlusion or pulmonary hypertension;
<50> the use of the above-mentioned <48>, wherein the blood flow disorder of skin is a blood flow disorder associated with pressure ulcer; and
<51> the use of the above-mentioned <48>, wherein the blood flow disorder of brain is a blood flow disorder associated with suppression of recurrence after cerebral infarction.

The present invention is explained in more detail in the following by referring to Reference Examples, Examples, Preparation Examples and Experimental Examples. The present invention is not limited by these Examples and the like and may be changed within the scope of the present invention.

Unless otherwise specified, the apparatuses, reagents and the like used in the present Examples and the like are easily obtained or prepared according to the methods generally conducted in the pertinent technical field, or commercially available.

In the following Reference Examples and Examples, the "room temperature" is generally about 10° C. to about 30° C. Unless otherwise specified, the ratios of mixed solvents are volume mixing ratios. % shows mol/mol % for yield and wt % for others.

The following abbreviations are used in the Reference Examples and Examples.
Me: methyl
Et: ethyl
Pr: propyl
Bu: butyl
Ph: phenyl
Ac: acetyl THP: tetrahydro-2H-pyran-2-yl
TBS: tert-butyldimethylsilyl
KHMDS: potassium bistrimethylsilylamide
DBU: 1,8-diazabicyclo[5.4.0]undec-7-ene
DMAP: 4-dimethylaminopyridine
Py: pyridine
DMSO: dimethyl sulfoxide
DME: 1,2-dimethoxyethane
p-TsOH: p-toluenesulfonic acid
aq: aqueous solution Reference Example 1: methyl (S)-5-cyclopropyl-2-methylpent-4-ynoate

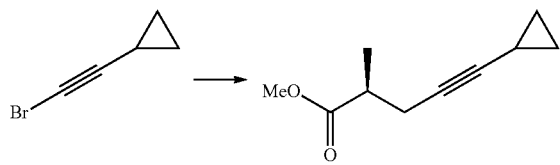

Lithium chloride (4.24 g) and zinc powder (9.15 g) were dried under reduced pressure, and tetrahydrofuran (THF) (100 mL), 1,2-dibromoethane (0.433 mL) and trimethylchlorosilane (0.127 mL) were added thereto at room temperature. To the mixture was added dropwise a solution of methyl (R)-3-iodo-2-methylpropionate (22.8 q) in THF (30 mL), and the mixture was stirred at 40° C. for 1.5 hr to prepare an organozinc reagent. In another reaction container were added lithium chloride (7.63 g), copper(I) cyanide (8.06 g) and THF (90 mL), and the mixture was stirred for 1 hr. The mixture was cooled to −10° C., and the aforementioned organo zinc reagent was added dropwise thereto. The reaction mixture was stirred at −10° C. for 10 min, cooled to −78° C., and a solution of 2-(bromoethynyl)cyclopropane (14.5 g) in THF (50 mL) was added dropwise. The mixture was stirred at the same temperature for 15 hr and poured into an aqueous ammonium chloride solution, and the mixture was extracted with ethyl acetate. The organic layer was washed with water, and the insoluble material was filtered off and washed with ethyl acetate. The filtrate was concentrated under reduced pressure, and the residue was purified by silica gel column chromatography (diethyl ether:hexane=1:30-1:5) to give the title compound (9.93 g). Yield: 66%.

$^1$H NMR (400 MHz, CDCl$_3$) δ 3.69 (s, 3H), 2.59 (dq, J=6.8, 7.2 Hz, 1H), 2.46 (ddd, J=2.0, 6.0, 16.4 Hz, 1H), 2.29 (ddd, J=2.0, 7.8, 16.4 Hz, 1H), 1.23 (d, J=7.2 Hz, 3H), 1.22 (m, 1H), 0.71 (m, 2H), 0.60 (m, 2H).

Reference Example 2: dimethyl (S)-(+)-(6-cyclopropyl-3-methyl-2-oxohex-5-yn-1-yl)phosphonate

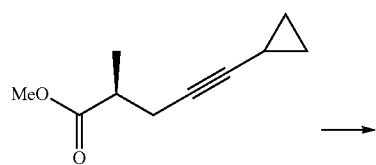

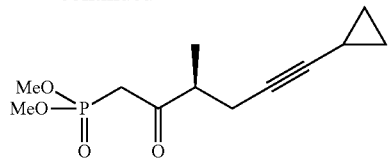

THF (25 mL) was added to dimethyl methylphosphonate (4.34 mL), and 1.6 M n-butyllithium (23.7 mL) was added dropwise thereto at −78° C. The reaction mixture was stirred at −78° C. for 1 hr, a solution of methyl (S)-5-cyclopropyl-2-methylpent-4-ynoate obtained in Reference Example 1 in THF (10 mL) was added thereto, and the mixture was stirred at the same temperature for 4 hr. To the reaction mixture was added an aqueous ammonium chloride solution, and the mixture was extracted with ethyl acetate, dried over anhydrous magnesium sulfate, and concentrated under reduced pressure. The residue was purified by silica gel column chromatography (ethyl acetate:hexane=1:3—ethyl acetate alone) to give the title compound (2.36 g). Yield: 61%.

$^1$H NMR (400 MHz, CDCl$_3$) δ 3.81 (s, 3H), 3.78 (s, 3H), 3.20 (ddd, J=14.4, 22.8, 28.4 Hz, 2H), 2.91 (q, J=6.8 Hz, 1H), 2.33 (dddd, J=2.0, 6.8, 16.8, 44.4 Hz, 2H), 1.18 (d, J=7.2 Hz, 3H), 1.18 (m, 1H), 0.71 (m, 2H), 0.60 (m, 2H).

Reference Example 3: methyl 7-((1R,2R,3R,5S)-5-acetoxy-2-hydroxymethyl-3-((tetrahydro-2H-pyran-2-yl)oxy)cyclopentyl)heptanoate

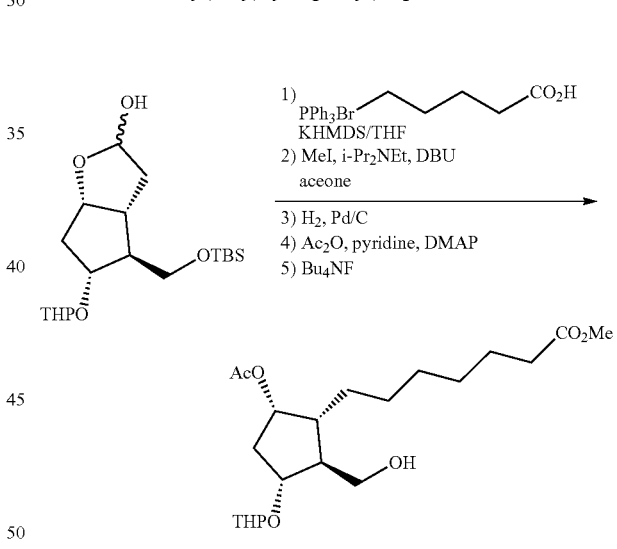

To a suspension of 4-(carboxybutyl)triphenylphosphonium bromide (14.06 g) in THF (86 mL) was added 1M potassium bistrimethylsilylamide (64 mL), and the mixture was stirred for 1 hr. The mixture was cooled to −78° C., and a solution of (3aR,4S,5R,6aS)-4-(((tert-butyldimethylsilyl)oxy)methyl)hexahydro-5-((tetrahydro-2H-pyran-2-yl)oxy)-2H-cyclopenta[b]furan-2-ol (3.92 g) in THF (50 mL) was added thereto. The mixture was stirred at the same temperature for 30 min, heated to room temperature, and stirred overnight. Water was added to the reaction mixture, and the mixture was extracted with tert-butylmethylether, acidified with disodium citrate, and extracted with ethyl acetate. The organic layer was dried over anhydrous sodium sulfate and concentrated under reduced pressure, and acetone (390 mL) was added thereto. Diisopropylethylamine (9.16 mL), iodomethane (2.95 mL) and 1,8-diazabicyclo[5.4.0]undec- 7-ene (7.85 mL) were added thereto at 0° C. The mixture was stirred at room temperature for 3.5 hr, saturated aqueous sodium hydrogen carbonate was added thereto, and the mixture was extracted with ethyl acetate. After concentration under reduced pressure, the residue was purified by silica gel column chromatography to give a viscous oil (3.21 g). Methanol (220 mL) was added to the oil (3.13 g), and the mixture was stirred using 5% Pd/C (1.13 g) under a hydrogen atmosphere for 40 min. The catalyst was filtered off, and the filtrate was concentrated under reduced pressure. To the residue were added pyridine (14 mL), acetic anhydride (14 mL), and 4-dimethylaminopyridine (170 mg), and the mixture was stirred for 1 hr. Water was added to the reaction mixture, and the mixture was extracted with a hexane-ethyl acetate mixed solvent. The organic layer was dried over anhydrous sodium sulfate and concentrated under reduced pressure. THF (32 mL) was added to the residue, and the mixture was ice-cooled. 1M tetrabutylammonium fluoride (6.7 mL) was added thereto, and the mixture was stirred at room temperature for 3 days. The reaction mixture was concentrated under reduced pressure, and the residue was purified by silica gel column chromatography (hexane:ethyl acetate=3:1-1:3) to give the title compound (2.60 g).

¹H NMR (300 MHz, CDCl₃) δ 5.07 (m, 1H), 4.71 (m, 0.55H), 4.54 (m, 0.45H), 4.15-4.04 (m, 1H), 4.04-3.88 (m, 1H), 3.88-3.73 (m, 2H), 3.66 (s, 3H), 3.60-3.48 (m, 2H), 2.29 (m, 2H), 2.04 (t, J=7.5 Hz, 2H), 1.95-1.15 (m, 20H).

Reference Example 4: methyl 7-((1R,2R,3R,5S)-5-acetoxy-2-formyl-3-((tetrahydro-2H-pyran-2-yl)oxy)cyclopentyl)heptanoate

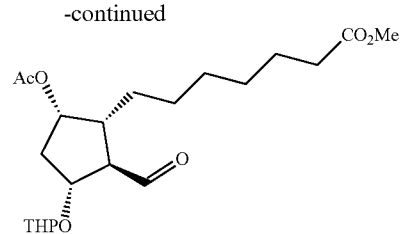

Methyl 7-((1R,2R,3R,5S)-5-acetoxy-2-hydroxymethyl-3-((tetrahydro-2H-pyran-2-yl)oxy)cyclopentyl)heptanoate (3.0 g) was dissolved in ethyl acetate (48 mL), and N,N-diisopropylethylamine (7.6 mL) was added thereto under ice-cooling. To the mixture was added a solution of SO₃-pyridine (3.6 g) in dimethylsulfoxide (24 mL), and the mixture was stirred for 30 min under ice-cooling. The reaction mixture was poured into ethyl acetate (50 mL) and water (50 mL), partitioned by adding aqueous sodium hydrogen carbonate, and the organic layer was concentrated under reduced pressure. Hexane was added to the residue, and the mixture was washed successively with an aqueous copper sulfate solution, saturated brine and water. The organic layer was dried over anhydrous sodium sulfate and concentrated under reduced pressure to give the title compound (2.75 g).

¹H NMR (300 MHz, CDCl₃) δ 9.77 (dd, J=16.1, 3.2 Hz, 1H), 5.13 (m, 1H), 4.70-4.50 (m, 1H), 4.41 (m, 1H), 3.81 (m, 2H), 3.66 (s, 3H), 3.46 (m, 2H), 3.40-2.92 (m, 0.46H), 2.88-2.78 (m, 0.54H), 2.28 (t, J=7.5 Hz, 2H), 2.50-2.20 (m, 1H), 2.06 (s, 3H), 1.98-1.52 (m, 16H).

Reference Example 5: methyl 7-((1R,2R,3R,5S)-5-acetoxy-2-((1E,4S)-7-cyclopropyl-4-methyl-3-oxo-hept-1-en-6-yn-1-yl)-3-((tetrahydro-2H-pyran-2-yl)oxy)cyclopentyl)heptanoate

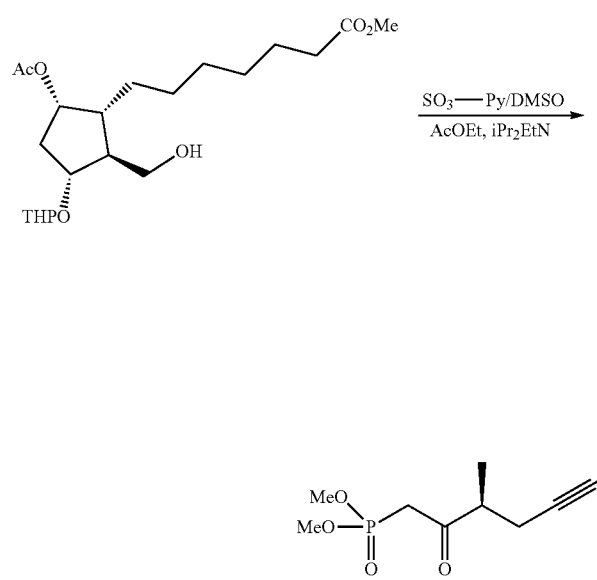

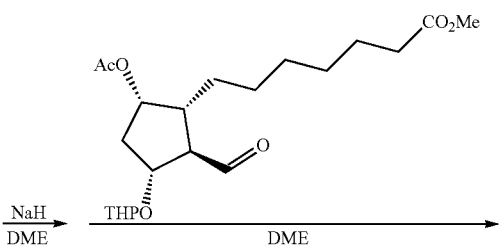

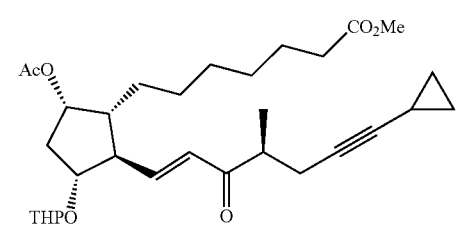

To sodium hydride (60%, dispersion in oil) (575 mg) was added 1,2-dimethoxyethane (126 mL), and a solution of dimethyl (S)-(+)-(6-cyclopropyl-3-methyl-2-oxohex-5-yn-1-yl)phosphonate (3.41 g) synthesized in Reference Example 2 in 1,2-dimethoxyethane (20 mL) was added dropwise thereto under ice-cooling. The mixture was stirred under ice-cooling for 1 hr, a solution of methyl 7-((1R,2R,3R,5S)-5-acetoxy-2-formyl-3-((tetrahydro-2H-pyran-2-yl)oxy)cyclopentyl)heptanoate (2.75 g) synthesized in Reference Example 4 in 1,2-dimethoxyethane (40 mL) was added dropwise thereto, and the mixture was stirred at the same temperature for 3 hr. To the reaction mixture were added ethyl acetate (290 mL) and saturated brine (290 mL), the mixture was diluted with water to carry out a liquid separation, and the aqueous layer was extracted with ethyl acetate. The organic layer was dried over anhydrous sodium sulfate and concentrated under reduced pressure, and the residue was purified by silica gel column chromatography (hexane:ethyl acetate=86:14—ethyl acetate alone) to give the title compound (3.43 g) as a colorless oil. Yield: 61% (2 step yield from methyl 7-((1R,2R,3R,5S)-5-acetoxy-2-hydroxymethyl-3-((tetrahydro-2H-pyran-2-yl)oxy)cyclopentyl)heptanoate obtained in Reference Example 3).

$^1$H NMR (400 MHz, CDCl$_3$) δ 6.80 (m, 1H), 6.28 (m, 1H), 5.12 (brt, J=5.7 Hz, 1H), 4.54 (dt, J=12.8, 3.0 Hz, 1H), 4.12-3.96 (m, 1H), 3.83-3.58 (m, 2H), 3.65 (s, 3H), 3.50-3.38 (m, 1H), 3.14-2.83 (m, 1H), 2.75-2.16 (m, 4H), 2.06 (s, 3H), 1.95-1.05 (m, 20H), 1.18 (d, J=7.2 Hz, 3H), 0.75-0.54 (m, 4H).

Reference Example 6: methyl 7-((1R,2R,3R,5S)-5-acetoxy-2-((1E,3S,4S)-7-cyclopropyl-3-hydroxy-4-methylhept-1-en-6-yn-1-yl)-3-hydroxycyclopentyl)heptanoate

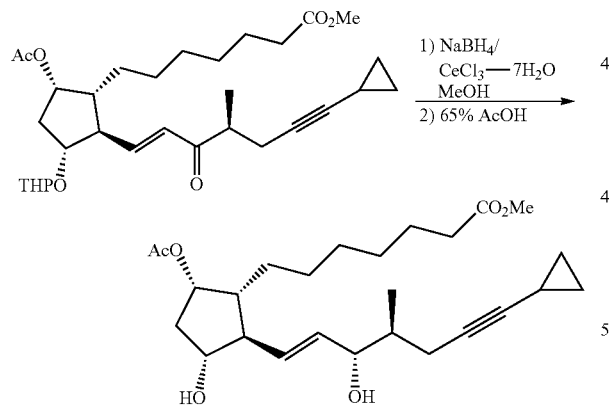

Methyl 7-((1R,2R,3R,5S)-5-acetoxy-2-((1E,4S)-7-cyclopropyl-4-methyl-3-oxohept-1-en-6-yn-1-yl)-3-(tetrahydro-2H-pyran-2-yl)oxy)cyclopentyl)heptanoate (2.47 g) synthesized in Reference Example 5 was dissolved in methanol (42 mL), cerium chloride heptahydrate (1.74 g) was added thereto, and the mixture was cooled to −40° C. To the mixture was added sodium borohydride (90.2 mg), and the mixture was stirred at the same temperature for 75 min. The reaction mixture was diluted with ethyl acetate, partitioned by adding saturated aqueous sodium hydrogen carbonate and water, and the aqueous layer was extracted with ethyl acetate. The organic layers were combined, washed with saturated brine, dried over anhydrous sodium sulfate, and concentrated under reduced pressure to give the title compound (2.45 g) as a crude product.

$^1$H NMR (400 MHz, CDCl$_3$) δ 5.65-5.45 (m, 2H), 5.09 (brs, 1H), 4.60 (m, 1H), 4.14-3.98 (m, 1H), 3.92-3.78 (m, 2H), 3.66 (s, 3H), 2.60-2.30 (m, 1H), 2.28 (t, J=7.6 Hz, 2H), 2.30-2.13 (m, 2H), 2.04 (s, 3H), 1.85-1.10 (m, 23H), 0.96 (m, 3H), 0.72-0.58 (m, 4H).

The aforementioned crude product (2.45 g) was dissolved in THF (9.3 mL), a 65% aqueous acetic acid solution (93 mL) was added thereto, and the mixture was stirred at 45° C. for 2 hr. The reaction mixture was allowed to cool to room temperature, water (100 mL) was added thereto, and the mixture was extracted with an ethyl acetate-hexane (1:1) mixed solvent. The organic layers were combined, dried over anhydrous sodium sulfate, and concentrated under reduced pressure. The residue was purified by silica gel column chromatography (hexane:ethyl acetate=67:33—ethyl acetate alone) to give the title compound (723 mg) and a stereoisomer thereof (1.23 g).

$^1$H NMR (400 MHz, CDCl$_3$)

The title compound: δ 5.58 (dd, J=15.2, 7.4 Hz, 1H), 5.45 (dd, J=15.2, 9.2 Hz, 1H), 5.14 (brt, J=4.6 Hz, 1H), 3.97 (t, J=7.4 Hz, 1H), 3.87 (q, J=8.5 Hz, 1H), 3.66 (s, 3H), 2.72-2.56 (m, 2H), 2.50 (dq, J=8.5, 6.5 Hz, 1H), 2.28 (t, J=7.6 Hz, 2H), 2.30-2.17 (m, 2H), 2.05 (s, 3H), 1.80-1.49 (m, 6H), 1.49-1.00 (m, 9H), 0.93 (d, J=6.5 Hz, 3H), 0.75-0.68 (m, 2H), 0.62-0.57 (m, 2H).

Isomer of the title compound: δ 5.61 (dd, J=15.2, 5.6 Hz, 1H), 5.50 (dd, J=15.2, 8.6 Hz, 1H), 5.15 (brt, J=4.6 Hz, 1H), 4.18 (t, J=4.8 Hz, 1H), 3.90 (m, 1H), 3.65 (s, 3H), 2.48 (dq, J=8.6, 6.4 Hz, 1H), 2.28 (t, J=7.6 Hz, 2H), 2.05 (s, 3H), 1.86-1.17 (m, 10H), 1.49-1.00 (m, 9H), 0.96 (d, J=6.4 Hz, 3H), 0.72-0.68 (m, 2H), 0.62-0.58 (m, 2H).

Reference Example 7: 7-((1R,2R,3R,5S)-2-((1E,3S,4S)-7-cyclopropyl-4-methyl-3-((tetrahydro-2H-pyran-2-yl)oxy) hept-1-en-6-yn-1-yl)-5-hydroxy-3-((tetrahydro-2H-pyran-2-yl)oxy)cyclopentyl) heptanoic acid

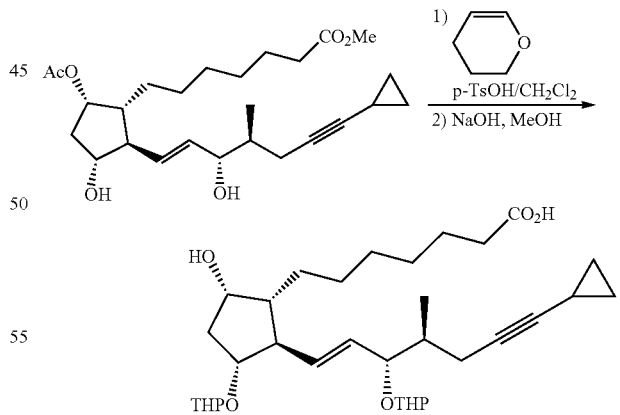

Methyl 7-((1R,2R,3R,5S)-5-acetoxy-2-((1E,3S,4S)-7-cyclopropyl-3-hydroxy-4-methylhept-1-en-6-yn-1-yl)-3-hydroxycyclopentyl)heptanoate (67.6 mg) synthesized in Reference Example 6 was dissolved in methylene chloride (1 mL), 3,4-dihydro-2H-pyran (41.3 μL) and p-toluenesulfonic acid monohydrate (2.9 mg) were added thereto at 0° C., and the mixture was stirred at the same temperature for 30 min. To the reaction mixture were added diethylether (10 mL) and saturated aqueous sodium hydrogen carbonate (10 mL), the mixture was partitioned, and the aqueous layer was extracted with diethylether. The organic layers were combined, dried over anhydrous sodium sulfate, and concentrated under reduced pressure to give acetoxy-bis tetrahydropyranyl (THP) ether form (117.1 mg) as a crude product.

$^1$H NMR (400 MHz, CDCl$_3$) δ 5.56-5.26 (m, 2H), 5.10 (m, 1H), 4.81-4.58 (m, 2H), 4.20-3.80 (m, 6H), 3.65 (s, 3H), 3.48-3.40 (m, 2H), 2.60-2.31 (m, 1H), 2.28 (t, J=7.6 Hz, 2H), 2.31-2.10 (m, 3H), 2.04 (s, 3H), 1.90-1.10 (m, 22H), 0.93 (m, 3H), 0.70-0.68 (m, 2H), 0.62-0.58 (m, 2H).

The crude product (117 mg) of acetoxy-bis THP ether form obtained above was dissolved in methanol (0.7 mL), a 1N aqueous sodium hydroxide solution (0.45 mL) was added thereto at 0° C., and the mixture was stirred at room temperature for 26 hr. To the reaction mixture was added an aqueous citric acid solution, and the mixture was extracted with ethyl acetate. The organic layers were combined, dried over anhydrous magnesium sulfate, and concentrated under reduced pressure, and the residue was purified by silica gel column chromatography (hexane:ethyl acetate=1:1-1:3) to give the title compound (70.9 mg).

$^1$H NMR (400 MHz, CDCl$_3$) δ 5.55-5.25 (m, 2H), 4.71 (m, 2H), 4.15-3.84 (m, 6H), 3.47 (m, 2H), 2.50-2.35 (m, 1H), 2.34 (t, J=7.2 Hz, 2H), 2.25-2.10 (m, 2H), 1.97-1.20 (m, 28H), 0.94 (m, 3H), 0.71-0.68 (m, 2H), 0.60-0.58 (m, 2H).

Reference Example 8: methyl 7-((1R,2R,3R,5S)-2-((1E,3S,4S)-7-cyclopropyl-4-methyl-3-((tetrahydro-2H-pyran-2-yl)oxy)hept-1-en-6-yn-1-yl)-5-hydroxy-3-((tetrahydro-2H-pyran-2-yl)oxy)cyclopentyl)heptanoate

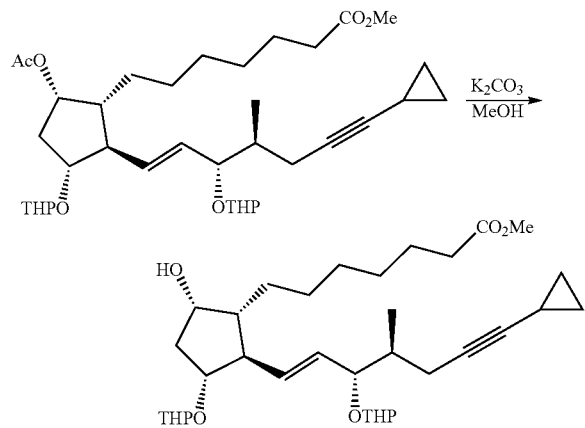

To acetoxy-bis THP ether form synthesized in the same manner as in Reference Example 7 (682.4 mg) were added methanol (6 mL) and potassium carbonate (382.8 mg), and the mixture was stirred at 40° C. for 2 hr. The reaction mixture was allowed to cool to room temperature, diluted with ethyl acetate, neutralized with acetic acid, and partitioned by adding saturated aqueous sodium hydrogen carbonate. The organic layer was washed with saturated brine, dried over anhydrous sodium sulfate, and concentrated under reduced pressure, and the residue was purified by silica gel column chromatography (hexane:ethyl acetate=84:16—ethyl acetate alone) to give the title compound (566.6 mg).

$^1$H NMR (400 MHz, CDCl$_3$) δ 5.58-5.42 (m, 1.5H), 5.28-5.18 (m, 0.5H), 4.77-4.60 (m, 2H), 4.18-4.08 (m, 2H), 3.90-3.75 (m, 3H), 3.66 (s, 3H), 3.51-3.38 (m, 2H), 2.50-2.00 (m, 5H), 2.29 (t, J=7.4 Hz, 2H), 2.00-1.40 (m, 26H), 0.92 (dddd, J=17.2, 17.2, 6.8, 6.8 Hz, 3H), 0.74-0.68 (m, 2H), 0.62-0.58 (m, 2H).

Reference Example 9: (2E)-7-((1R,2R,3R,5S)-2-((1E,3S,4S)-7-cyclopropyl-4-methyl-3-((tetrahydro-2H-pyran-2-yl)oxy)hept-1-en-6-yn-1-yl)-5-hydroxy-3-((tetrahydro-2H-pyran-2-yl)oxy)cyclopentyl)hept-2-enoic acid

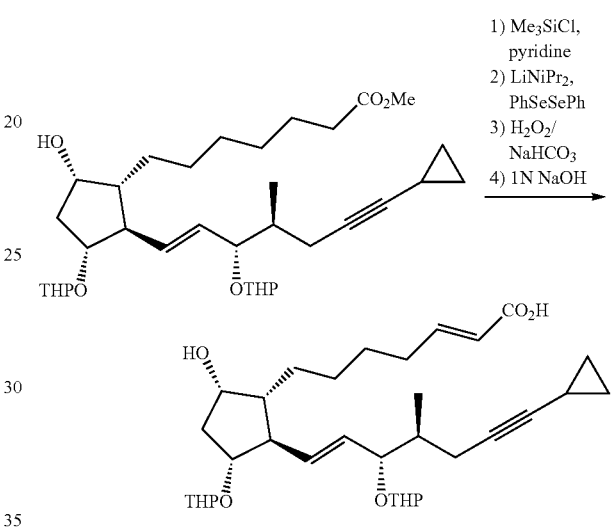

To methyl 7-((1R,2R,3R,5S)-2-((1E,3S,4S)-7-cyclopropyl-4-methyl-3-((tetrahydro-2H-pyran-2-yl)oxy)hept-1-en-6-yn-1-yl)-5-hydroxy-3-((tetrahydro-2H-pyran-2-yl)oxy)cyclopentyl)heptanoate (364.4 mg) synthesized in Reference Example 8 was added pyridine (2 mL), and the mixture was cooled to 0° C. Trimethylchlorosilane (0.12 mL) was added thereto, and the mixture was stirred at the same temperature for 30 min. The reaction mixture was diluted with a mixed solvent of hexane and ethyl acetate (10:1), partitioned by adding saturated aqueous sodium hydrogen carbonate, and the organic layer was washed successively with water and saturated brine. The organic layer was dried over anhydrous sodium sulfate and concentrated under reduced pressure to give silylether form (366.1 mg) as a crude product.

The crude product (366.1 mg) of silylether form was dissolved in THF (2.5 mL), a THF solution (1.41 mL) of 1.12 M lithium diisopropylamide was added thereto at −78° C., and the mixture was stirred at the same temperature for 30 min. To the mixture was added dropwise a solution of diphenyldiselenide (412.9 mg) in THF (1 mL) at −78° C., and the mixture was stirred at the same temperature for 45 min and at 0° C. for 1 hr. The reaction mixture was diluted with ethyl acetate, partitioned by adding saturated ammonium chloride, and the aqueous layer was extracted with ethyl acetate. The organic layers were combined, washed with saturated brine, dried over anhydrous sodium sulfate, and concentrated under reduced pressure to give Selenylated form (763 mg) as a crude product.

To the crude product (763 mg) of the Selenylated form were added ethyl acetate (4 mL), THF (2 mL) and sodium hydrogen carbonate (179.2 mg), and the mixture was stirred. To the mixture was added 30% hydrogen peroxide water (0.21 mL), and the mixture was stirred at 35° C. for 1 hr. The reaction mixture was diluted with ethyl acetate, saturated aqueous sodium hydrogen carbonate was added thereto, and the mixture was extracted with ethyl acetate. The organic layers were combined, washed with saturated brine, dried over anhydrous sodium sulfate, and concentrated under reduced pressure. The residue was dissolved in methanol (5 mL), a 1N aqueous sodium hydroxide solution (1.9 mL) was added thereto at 0° C., and the mixture was stirred at room temperature for 43 hr. The reaction mixture was diluted with ethyl acetate, neutralized with a saturated aqueous disodium citrate solution, and extracted with ethyl acetate. The extract was dried over anhydrous sodium sulfate, concentrated under reduced pressure, and purified by silica gel column chromatography (hexane:ethyl acetate=3:1—ethyl acetate—ethyl acetate:methanol=20:1) to give the title compound (169.8 mg).

$^1$H NMR (400 MHz, CDCl$_3$) δ 7.00-6.87 (m, 1H), 5.81 (d, J=14.8 Hz, 1H), 5.63-5.41 (m, 2H), 5.30-5.18 (m, 1H), 4.82-4.60 (m, 2H), 4.20-3.52 (m, 6H), 3.72 (s, 3H), 3.53-3.39 (m, 2H), 2.59-1.00 (m, 25H), 0.92 (m, 3H), 0.74-0.63 (m, 2H), 0.60-0.52 (m, 2H).

Reference Example 10: methyl 7-((1R,2R,3R,5S)-5-acetoxy-2-((1E,4S)-4-methyl-3-oxonon-1-en-6-yn-1-yl)-3-((tetrahydro-2H-pyran-2-yl)oxy)cyclopentyl)heptanoate Reference Example 11: methyl 7-((1R,2R,3R,5S)-5-acetoxy-2-hydroxymethyl-3-((tetrahydro-2H-pyran-2-yl)oxy)cyclopentyl)-2,2-difluoroheptanoate

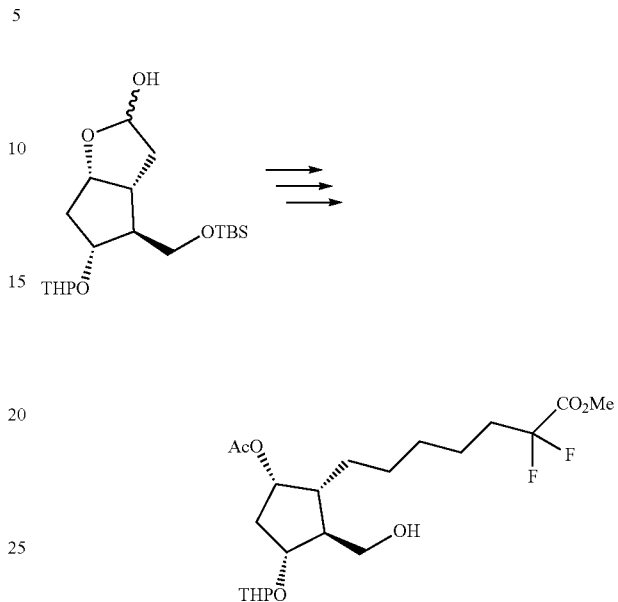

The title compound was synthesized in the same manner as in Reference Example 3 from (3aR,4S,5R,6aS)-4-(((tert-butyldimethylsilyl)oxy)methyl)hexahydro-5-((tetrahydro-

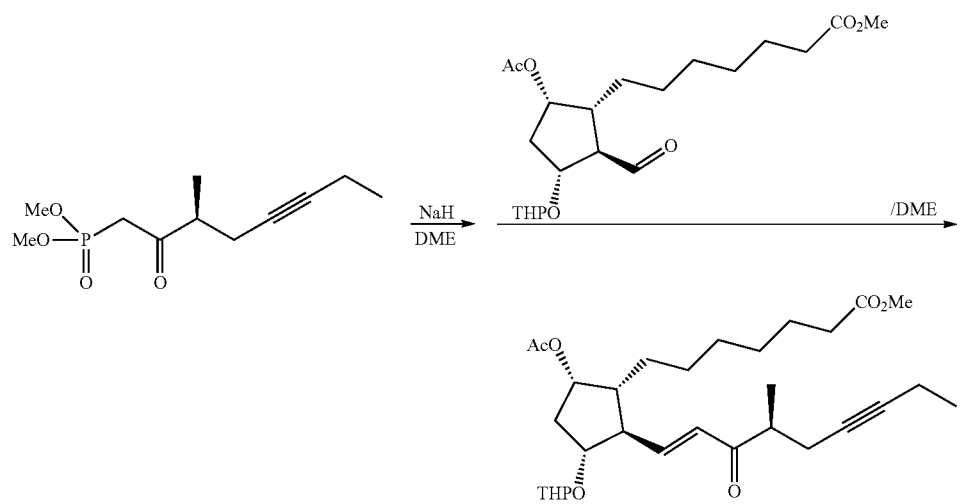

The title compound was synthesized in the same manner as in Reference Example 5 from dimethyl (S)-3-methyl-2-oxooct-5-yn-1-yl)phosphonate and methyl 7-((1R,2R,3R,5S)-5-acetoxy-2-formyl-3-((tetrahydro-2H-pyran-2-yl)oxy)cyclopentyl)heptanoate synthesized in Reference Example 4.

$^1$H NMR (300 MHz, CDCl$_3$) δ 6.76 (m, 1H), 6.29 (m, 1H), 5.13 (m, 1H), 4.58 (m, 1H), 4.12-3.44 (m, 3H), 3.66 (s, 3H), 2.89 (m, 1H), 2.74-2.10 (m, 5H), 2.07 (s, 3H), 1.99-1.08 (m, 21H), 1.20 (d, J=7.2 Hz, 3H), 1.10 (t, J=7.4 Hz, 3H).

2H-pyran-2-yl)oxy)-2H-cyclopenta[b]furan-2-ol by using 4-(1-carboxy-2,2-difluorobutyl)triphenylphosphonium bromide instead of 4-(carboxybutyl)triphenylphosphonium bromide.

$^1$H NMR (300 MHz, CDCl$_3$) δ 5.64 (dt, J=5.2, 5.2, 2.0 Hz, 1H), 4.70 (dd, J=4.0, 0.8 Hz, 0.5H), 4.53 (dd, J=5.1, 2.4 Hz, 0.5H), 4.08 (dddd, J=8.4, 6.6, 4.8, 4.4 Hz, 0.5H), 4.53 (dd, J=8.0, 6.2, 4.4, 4.4 Hz, 0.5H), 3.96-3.71 (m, 2H), 3.85 (s, 3H), 3.58-3.43 (m, 2H), 3.00 (brs, 1H), 2.29 (m, 2H), 2.12-1.15 (m, 18H), 2.03 (s, 2.4 Hz, 3H). $^{19}$F NMR (282.65 MHz, CD$_3$OD) δ -106.26 (t, J=17.3 Hz, 2F).

Reference Example 12: 2-((1S,2R,3R,5S)-5-hydroxy-2-((1E,3RS, 4S)-4-methyl-3-((tetrahydro-2H-pyran-2-yl)oxy) non-1-en-6-yn-1-yl)-3-((tetrahydro-2H-pyran-2-yl)oxy)cyclopentyl)ethanol

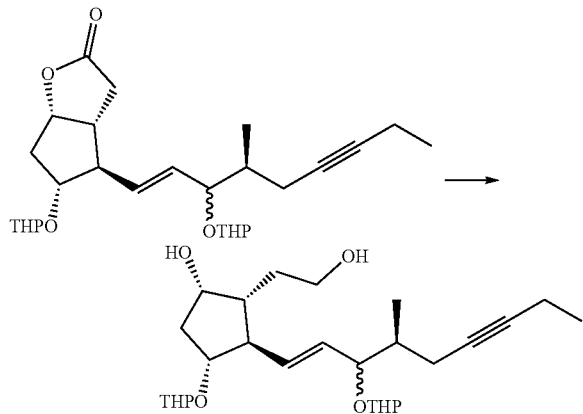

(3aR,4R,5R,6aS)-hexahydro-5-hydroxy-4-((1E,3RS,4S)-3-hydroxy-4-methyl-1-nonen-6-ynyl)-2H-cyclopenta[b]furan-2-one (3.50 g) was dissolved in methylene chloride (61 mL), 2,3-dihydropyran (3.3 mL) and p-toluenesulfonic acid monohydrate (24.5 mg) were added thereto under ice-cooling, and the mixture was stirred at room temperature for 30 min. The reaction mixture was poured into saturated aqueous sodium hydrogen carbonate, and the mixture was extracted with ethyl acetate. The organic layer was dried over anhydrous sodium sulfate and concentrated under reduced pressure, and the residue was purified by silica gel column chromatography (hexane:ethyl acetate=85/15—ethyl acetate) to give bis THP ether form (7.26 g). The bis THP ether form (994 mg) was dissolved in THF (4 mL) and added to a suspension of lithium aluminum hydride (75 mg) in THF (4 mL) under ice-cooling. The mixture was stirred at the same temperature for 40 min. The reaction mixture was diluted with diethylether, an aqueous sodium sulfate solution was added thereto, and the mixture was filtered through celite and washed with ethyl acetate. The filtrate was concentrated under reduced pressure to give the title compound (953 mg) as a viscous oil.

$^1$H NMR (300 MHz, CDCl$_3$) δ 5.60-5.26 (m, 2H), 4.77-4.65 (m, 2H), 4.30-3.60 (m, 7H), 3.48 (m, 2H), 2.20-1.40 (m, 25H), 1.13 (t, J=6.9 Hz, 3H), 0.96 (m, 3H).

Reference Example 13: methyl 4-((2-((1R,2R,3R,5S)-5-hydroxy-2-((1E,3RS,4S)-4-methyl-3-((tetrahydro-2H-pyran-2-yl)oxy)non-1-en-6-yn-1-yl)-3-((tetrahydro-2H-pyran-2-yl)oxy)cyclopentyl)ethyl)thio)butanoate

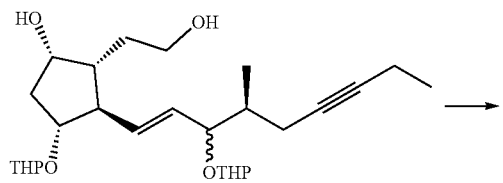

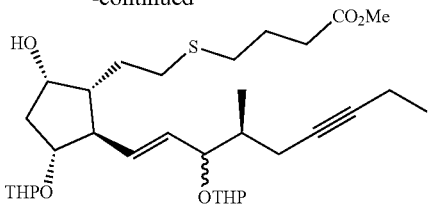

2-((1S,2R,3R,5S)-5-hydroxy-2-((1E,3RS,4S)-4-methyl-3-((tetrahydro-2H-pyran-2-yl)oxy)non-1-en-6-yn-1-yl)-3-((tetrahydro-2H-pyran-2-yl)oxy)cyclopentyl)ethanol (122 mg) synthesized in Reference Example 12 was dissolved in THF (2 mL), diisopropylethylamine (91 μL) and methanesulfonyl chloride (30 μL) were added thereto at −20° C., and the mixture was stirred for 1 hr. To the reaction mixture were added diisopropylethylamine (44 μL) and methanesulfonyl chloride (10 μL), and the mixture was stirred at −10° C. for 1 hr. Diisopropylamine (91 μL) and chlorotrimethylsilane (40 μL) were added thereto, and the mixture was stirred for 1 hr. Furthermore, a solution of S-potassium thioacetate (92 mg) in N,N-dimethylformamide (2.5 mL) was added thereto at −10° C., potassium carbonate (211 mg) was added thereto, and the mixture was stirred at room temperature overnight. Water was added to the reaction mixture, the mixture was extracted with a mixed solvent of ethyl acetate and hexane (1:1), and the organic layer was washed with saturated brine, dried over anhydrous sodium sulfate, and concentrated under reduced pressure. The residue was dissolved in methanol (1 mL), methyl 4-iodobutanoate (72 mg) and potassium carbonate (86 mg) were added thereto, and the mixture was stirred at room temperature for 1.5 hr. Thereafter, a saturated aqueous ammonium chloride solution was added thereto, the mixture was extracted with tert-butylmethylether, dried over anhydrous sodium sulfate, and concentrated under reduced pressure, and the residue was purified by silica gel column chromatography (hexane:ethyl acetate=4:1-1:1) to give the title compound (71 mg).

$^1$H NMR (300 MHz, CDCl$_3$) δ 5.55 (m, 2H), 4.68 (m, 2H), 4.30-3.70 (m, 5H), 3.67 (s, 3H), 3.46 (m, 2H), 2.60-2.40 (m, 4H), 2.23 (m, 2H), 2.10-1.40 (m, 26H), 1.13 (t, J=6.9 Hz, 3H), 0.96 (m, 3H).

Example 1: methyl 4-((2-((1R,2R,3R)-3-hydroxy-2-((1E,3RS,4S)-3-hydroxy-4-methylnon-1-en-6-yn-1-yl)-5-oxocyclopentyl)ethyl)thio)butanoate [Compound (1)-1]

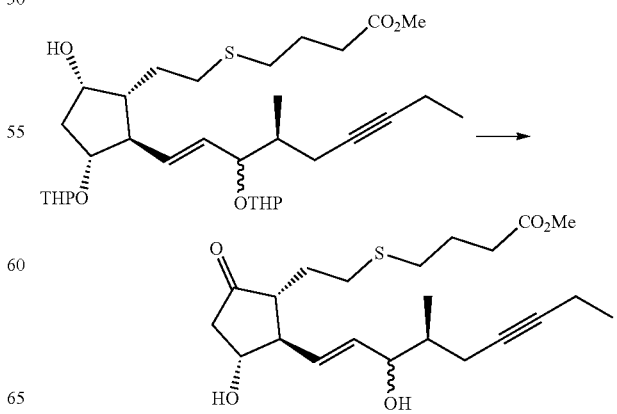

To methyl 4-((2-((1R,2R,3R,5S)-5-hydroxy-2-((1E,3RS,4S)-4-methyl-3-((tetrahydro-2H-pyran-2-yl)oxy)non-1-en-6-yn-1-yl)-3-((tetrahydro-2H-pyran-2-yl)oxy)cyclopentyl)ethyl)thio)butanoate (70 mg) synthesized in Reference Example 13 were added ethyl acetate (0.8 mL) and N,N-diisopropylethylamine (0.15 mL), a solution of SO₃-pyridine (63 mg) in dimethylsulfoxide (0.67 mL) was slowly added thereto at 0° C., and the mixture was stirred for 20 min. Thereafter, the mixture was diluted with ethyl acetate, and partitioned by adding water. The organic layer was washed with 1N hydrochloric acid and saturated aqueous sodium hydrogen carbonate, dried over anhydrous sodium sulfate, and concentrated under reduced pressure, and the residue was purified by silica gel column chromatography (hexane:ethyl acetate=93/7-20/80) to give the corresponding 5-oxo-bis THP ether form (52 mg). To the 5-oxo-bis THP ether form (52 mg) were added THF (0.2 mL) and 65% acetic acid (3.6 mL), and the mixture was stirred at 45° C. for 1 hr, diluted with water, and extracted with a mixed solvent of hexane and ethyl acetate (1:1). The organic layer was dried over anhydrous sodium sulfate and dried under reduced pressure, and the residue was purified by silica gel column chromatography (hexane:ethyl acetate=50:50-35:65) to give the title compound (29 mg).

¹H NMR (300 MHz, CDCl₃) δ 5.64 (dddd, J=15.1, 15.1, 8.0, 6.9 Hz, 2H), 4.12-4.03 (m, 2H), 3.70 (s, 1H), 3.68 (s, 2H), 2.76 (dd, J=7.5, 6.6 Hz, 1H), 2.62 (dt, J=7.2, 3.2 Hz, 2H), 2.51 (t, J=7.4 Hz, 2H), 2.43 (t, J=7.4 Hz, 2H), 2.39-2.10 (m, 7H), 2.10-1.61 (m, 7H), 1.12 (t, J=7.5 Hz, 3H), 0.97 (d, J=6.6 Hz, 3H).

Example 2: methyl (2E)-4-((2-((1R,2R,3R)-3-hydroxy-2-((1E,3RS,4S)-3-hydroxy-4-methylnon-1-en-6-yn-1-yl)-5-oxocyclopentyl)ethyl)thio)but-2-enoate [Compound (1)-2]

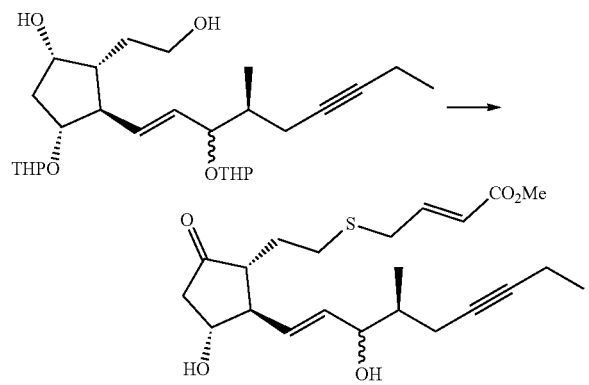

The title compound was obtained by synthesis in the same manner as in Reference Example 13 and Example 1 by using methyl 4-bromo-2-butenoate instead of methyl 4-iodobutanoate from 2-((1S,2R,3R,5S)-5-hydroxy-2-((E,3RS,4S)-4-methyl-3-((tetrahydro-2H-pyran-2-yl)oxy)non-1-en-6-yn-1-yl)-3-((tetrahydro-2H-pyran-2-yl)oxy)cyclopentyl)ethanol synthesized in Reference Example 12.

¹H NMR (300 MHz, CDCl₃) δ 6.86 (ddd, J=15.6, 7.6, 7.6 Hz, 1H), 6.07 (dt, J=15.6, 9.5 Hz, 1H), 5.92-5.56 (m, 2H), 4.30-4.00 (m, 2H), 3.75 (s, 3H), 3.60-3.00 (m, 2H), 2.90-2.70 (m, 2H), 2.70-2.08 (m, 9H), 2.05-1.64 (m, 4H), 1.13 (t, J=7.2 Hz, 3H), 1.02-0.95 (m, 3H).

Example 3: methyl ((1R,2R,3R)-3-hydroxy-2-((1E,3RS,4S)-3-hydroxy-4-methylnon-1-en-6-yn-1-yl)-5-oxocyclopentyl)heptanoate [Compound (1)-3]

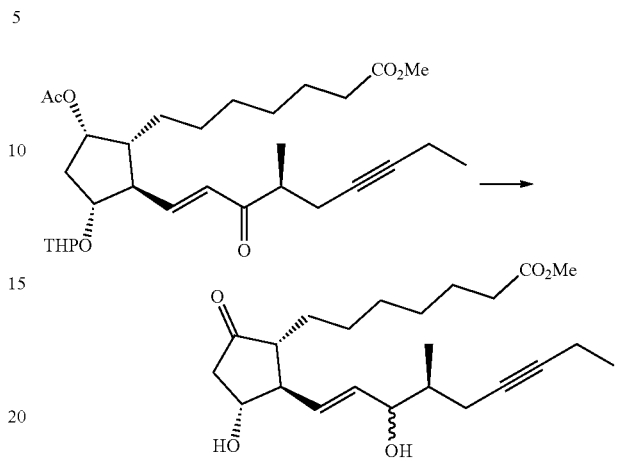

Methyl 7-((1R,2R,3R,5S)-5-acetoxy-2-((1E,4S)-4-methyl-3-oxonon-1-en-6-yn-1-yl)-3-((tetrahydro-2H-pyran-2-yl)oxy)cyclopentyl)heptanoate (44 mg) synthesized in Reference Example 10 was dissolved in methanol (0.5 mL), cerium chloride heptahydrate (9.5 mg) and sodium borohydride (1.9 mg) were added thereto under ice-cooling, and the mixture was stirred at room temperature for 30 min. The reaction mixture was diluted with ethyl acetate, partitioned by adding a saturated aqueous ammonium chloride solution, and the aqueous layer was extracted with ethyl acetate. The organic layers were combined, dried over anhydrous magnesium sulfate, and concentrated under reduced pressure. The residue was dissolved in methylene chloride (1 mL), 3,4-dihydro-2H-pyran (10.5 μL) and p-toluenesulfonic acid monohydrate (0.73 mg) were added thereto at 0° C., and the mixture was stirred at the same temperature for 1 hr. The reaction mixture was partitioned by adding ethyl acetate and saturated aqueous sodium hydrogen carbonate, and the aqueous layer was extracted with ethyl acetate. The organic layers were combined, dried over anhydrous magnesium sulfate, and concentrated under reduced pressure. To the residue were added methanol (0.5 mL) and potassium carbonate (10.6 mg), and the mixture was stirred at room temperature for 16 hr. The reaction mixture was partitioned by adding ethyl acetate and a saturated aqueous ammonium chloride solution, and the aqueous layer was extracted with ethyl acetate, dried over anhydrous magnesium sulfate, and concentrated under reduced 3c pressure. The residue was purified by silica gel column chromatography (hexane:ethyl acetate=84:16-50:50) to give methyl 7-((1R,2R,3R,5S)-2-((1E,3RS,4S)-4-methyl-3-((tetrahydro-2H-pyran-2-yl)oxy)non-1-en-6-yn-1-yl)-5-hydroxy-3-((tetrahydro-2H-pyran-2-yl)oxy)cyclopentyl)heptanoate (33 mg). The obtained compound was treated in the same manner as in Example 1 to give the title compound.

¹H NMR (300 MHz, CDCl₃) δ 5.75-5.55 (m, 2H), 4.22-3.98 (m, 2H), 3.66 (s, 3H), 2.75 (dd, J=18.4, 7.2 Hz, 1H), 2.43-1.28 (m, 22H), 1.12 (t, J=7.3 Hz, 3H) 0.97 (d, J=6.9 Hz, 3H).

Example 4: 7-((1R,2R,3R)-2-((1E,3S,4S)-7-cyclopropyl-3-hydroxy-4-methylhept-1-en-6-yn-1-yl)-3-hydroxy-5-oxocyclopentyl)heptanoic acid [Compound (1)-9]

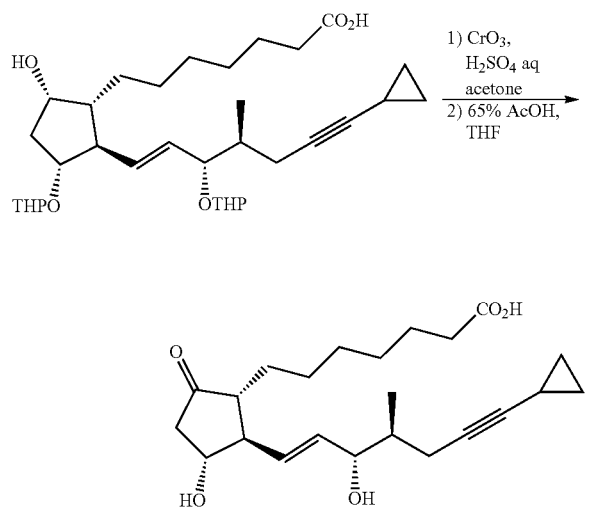

Example 5: (2E)-7-((1R,2R,3R)-2-((1E,3S,4S)-7-cyclopropyl-3-hydroxy-4-methylhept-1-en-6-yn-1-yl)-3-hydroxy-5-oxocyclopentyl)hept-2-enoic acid [Compound (1)-10]

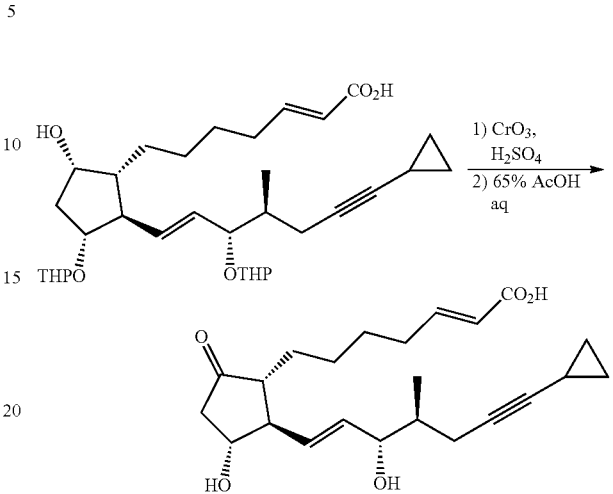

7-((1R,2R,3R,5S)-2-((1E,3S,4S)-7-cyclopropyl-4-methyl-3-((tetrahydro-2H-pyran-2-yl)oxy)hept-1-en-6-yn-1-yl)-5-hydroxy-3-((tetrahydro-2H-pyran-2-yl)oxy)cyclopentyl)heptanoic acid (70.9 mg) synthesized in Reference Example 7 was dissolved in acetone, and 2.67 M Jones reagent (70.8 μL) was added dropwise thereto at −20° C. The mixture was stirred at the same temperature for 30 min. Then, the Jones reagent (7.1 μL) was added thereto, and the mixture was further stirred for 10 min. The reaction mixture was partitioned by adding 2-propanol (0.15 mL), diethyl ether (10 mL) and water (6 mL). The aqueous layer was extracted with diethylether, and the organic layers were combined, washed successively with water and brine, dried over anhydrous magnesium sulfate, and concentrated under reduced pressure to give oxo-bis THP ether form (53.7 mg) as a crude product.

The obtained oxo-bis THP ether form as a crude product (53.7 mg) was dissolved in THF (0.252 mL), a 65% aqueous acetic acid solution (2.52 mL) was added thereto, and the mixture was stirred at 45° C. for 2 hr and at room temperature for 1 hr. Water was added to the reaction mixture, and the mixture was extracted with ethyl acetate. The organic layer was washed with saturated brine, dried over anhydrous magnesium sulfate, and concentrated under reduced pressure. The residue was purified by silica gel column chromatography (hexane:ethyl acetate=1:2—ethyl acetate alone—ethyl acetate:methanol=20:1) to give the title compound (29.5 mg).

$^1$H NMR (400 MHz, CDCl$_3$) δ 5.69 (dd, J=15.2, 7.6 Hz, 1H), 5.60 (dd, J=15.2, 8.8, 1H), 4.13-4.03 (m, 2H), 2.75 (dd, J=18.4, 7.2 Hz, 1H), 2.43-1.20 (m, 22H), 0.94 (d, J=6.4 Hz, 3H), 0.75-0.71 (m, 2H), 0.63-0.59 (m, 2H).

The title compound was synthesized by Jones oxidation followed by deTHP reaction in the same manner as in Example 4 by using (2E)-7-((1R,2R,3R,5S)-2-((1E,3S,4S)-7-cyclopropyl-4-methyl-3-((tetrahydro-2H-pyran-2-yl)oxy)hept-1-en-6-yn-1-yl)-5-hydroxy-3-((tetrahydro-2H-pyran-2-yl)oxy)cyclopentyl) hept-2-enoic acid synthesized in Reference Example 9. Yield: 66.4%.

$^1$H NMR (400 MHz, CDCl$_3$) δ 6.98 (dt, J=15.6, 6.9 Hz, 1H), 5.98 (brs, 2H), 5.77 (d, J=15.6 Hz, 1H), 5.58 (dddd, J=15.3, 15.3, 7.4, 6.8 Hz, 2H), 4.05-3.93 (m, 2H), 2.71 (dd, J=18.2, 7.4 Hz, 1H), 2.40-1.00 (m, 16H), 0.89 (d, J=6.8 Hz, 3H), 0.71-0.67 (m, 2H), 0.59-0.55 (m, 2H).

Example 6: 7-((1R,2R,3R)-3-hydroxy-2-((1E,3S,4S)-3-hydroxy-4-methylnon-1-en-6-yn-1-yl)-5-oxocyclopentyl)heptanoic acid [Compound (1)-6]

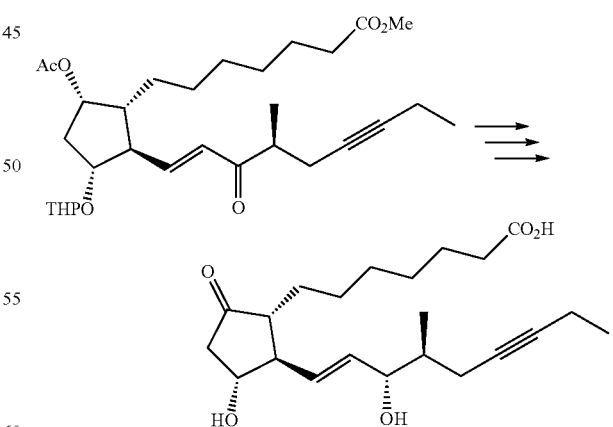

The title compound was synthesized in the same manner as in Reference Example 6, Reference Example 7 and Example 4 from methyl 7-((1R,2R,3R,5S)-5-acetoxy-2-((1E,4S)-4-methyl-3-oxonon-1-en-6-yn-1-yl)-3-((tetrahydro-2H-pyran-2-yl)oxy)cyclopentyl)heptanoate synthesized in Reference Example 10.

$^1$H NMR (400 MHz, CDCl$_3$) δ 5.65 (dddd, J=15.3, 15.3, 8.3, 7.2 Hz, 2H), 4.12-4.01 (m, 2H), 2.74 (dd, J=18.0, 7.2 Hz, 1H), 2.45-1.96 (m, 11H), 1.79 (m, 1H), 1.50-1.40 (m, 4H), 1.40-1.30 (m, 7H), 1.13 (t, J=6.9 Hz, 3H), 0.96 (d, J=6.9 Hz, 3H).

Example 7: (2E)-7-((1R,2R,3R)-3-hydroxy-2-((1E, 3S,4S)-3-hydroxy-4-methylnon-1-en-6-yn-1-yl)-5-oxocyclopentyl)hept-2-enoic acid [Compound (1)-7]

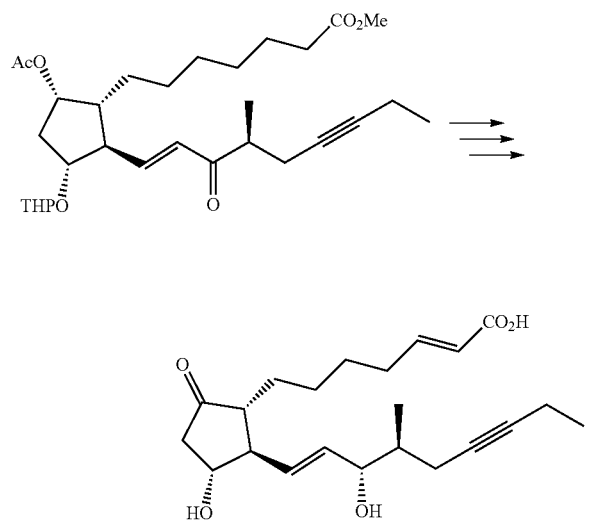

The title compound was synthesized in the same manner as in Reference Example 6, Reference Example 7, Reference Example 8, Reference Example 9 and Example 5 from methyl 7-((1R,2R,3R,5S)-5-acetoxy-2-((1E,4S)-4-methyl-3-oxonon-1-en-6-yn-1-yl)-3-((tetrahydro-2H-pyran-2-yl)oxy)cyclopentyl)heptanoate synthesized in Reference Example 10.

$^1$H NMR (300 MHz, CDCl$_3$) δ 7.01 (dt, J=15.4, 7.0 Hz, 1H), 5.80 (d, J=15.4 Hz, 1H), 5.62 (dddd, J=15.3, 15.3, 8.2, 7.7 Hz, 2H), 4.08-3.80 (m, 2H), 2.73 (dd, J=18.3, 7.5 Hz, 1H), 2.46-1.70 (m, 11H), 1.87-1.30 (m, 8H), 1.14 (t, J=7.4 Hz, 3H), 0.94 (t, J=6.9 Hz, 3H).

Example 8: (5-methyl-2-oxo-1,3-dioxol-4-yl)methyl 7-((1R,2R,3R)-3-hydroxy-2-((1E,3S,4S)-3-hydroxy-4-methylnon-1-en-6-yn-1-yl)-5-oxocyclopentyl)heptanoate [Compound (1)-4]

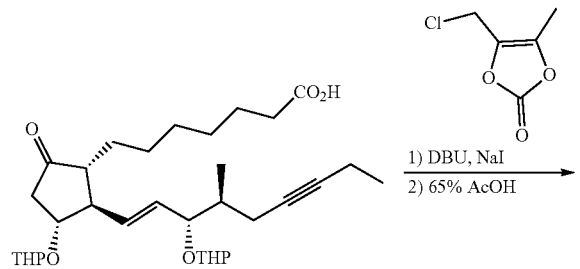

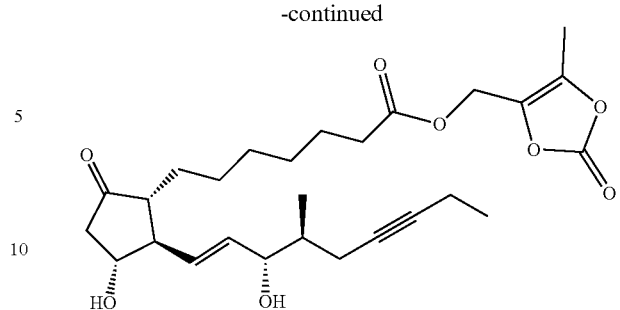

The oxo-bis THP ether form (250 mg) obtained as an intermediate in Example 6 in the same manner as in Example 4 was dissolved in acetone (4.5 mL), and 4-chloromethyl-5-methyl-1,3-dioxol-2-one (20.8 mg) was added dropwise thereto at 0° C. Sodium iodide (68.4 mg) and 1,8-diazabicyclo[5.4.0]undec-7-ene (82.2 mg) were added thereto, and the mixture was stirred at the same temperature for 21 hr. To the reaction mixture were added diethylether and saturated aqueous sodium hydrogen carbonate, and the aqueous layer was extracted with diethylether, dried over anhydrous sodium sulfate, and concentrated under reduced pressure. The residue was purified by silica gel column chromatography (hexane alone—hexane:ethyl acetate=16:84—ethyl acetate alone—ethyl acetate:methanol=98:2) to give ester form (278 mg). Then, THF (0.95 mL) and a 65% aqueous acetic acid solution (9.5 mL) were added to the obtained ester form (278 mg), and the mixture was stirred at 45° C. for 1 hr. Water was added to the reaction mixture, and the mixture was extracted with ethyl acetate. The organic layer was washed with saturated brine, dried over anhydrous magnesium sulfate, and concentrated under reduced pressure. The residue was purified by silica gel column chromatography (hexane:ethyl acetate=3:1-1:5—ethyl acetate alone—ethyl acetate:methanol=50:1) to give the title compound (168.2 mg).

$^1$H NMR (300 MHz, CDCl$_3$) δ 5.64 (dddd, J=15.2, 15.2, 8.4, 7.1 Hz, 2H), 4.83 (s, 2H), 4.13-3.99 (m, 2H), 2.74 (dd, J=17.7, 7.5 Hz, 1H), 2.46-1.94 (m, 11H), 1.85-1.19 (m, 14H), 1.13 (d, J=7.4 Hz, 3H), 0.95 (d, J=4.2 Hz, 3H).

Example 9: 3,3-dimethyl-2-oxobutyl 7-((1R,2R, 3R)-3-hydroxy-2-((1E,3S,4S)-3-hydroxy-4-methylnon-1-en-6-yn-1-yl)-5-oxocyclopentyl) heptanoate [Compound (1)-5]

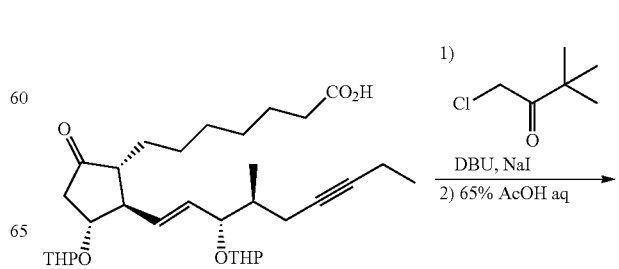

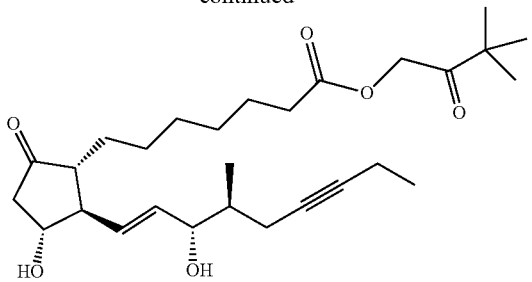

The oxo-bis THP ether form (200.9 mg) obtained as an intermediate in Example 6 in the same manner as in Example 4 was dissolved in acetone (3.7 mL), and 1-chloropinacolone (28.2 mg), sodium iodide (14 mg) and 1,8-diazabicyclo[5.4.0]undec-7-ene (16.6 mg) were added thereto at 0° C., and the mixture was stirred at the same temperature for 17 hr. To the reaction mixture were added diethylether and saturated aqueous sodium hydrogen carbonate, and the aqueous layer was extracted with diethylether. The organic layer was dried over anhydrous sodium sulfate, and concentrated under reduced pressure. The residue was purified by silica gel column chromatography (hexane alone—hexane:ethyl acetate=16:84—ethyl acetate alone—ethyl acetate:methanol=95:5) to give ester form (163.6 mg). Then, THF (0.95 mL) and a 65% aqueous acetic acid solution (9.5 mL) were added to the obtained ester form (21.6 mg), and the mixture was stirred at 45° C. for 2.5 hr. Water was added to the reaction mixture, and the mixture was extracted with ethyl acetate. The organic layer was washed with saturated brine, dried over anhydrous magnesium sulfate, and concentrated under reduced pressure. The residue was purified by silica gel column chromatography (hexane:ethyl acetate=3:1—ethyl acetate alone) to give the title compound (116.6 mg).

$^1$H NMR (300 MHz, CDCl$_3$) δ 5.76-5.57 (m, 2H), 4.88 (s, 2H), 4.18-4.00 (m, 2H), 2.82-2.68 (m, 1H), 2.46-1.95 (m, 10H), 1.85-1.17 (m, 12H), 1.21 (d, J=4.7 Hz, 9H), 1.14 (dt, J=7.4, 4.7 Hz, 3H), 0.97 (dd, J=6.9, 4.5 Hz, 3H).

Example 10: 2,2-difluoro-7-((1R,2R,3R)-3-hydroxy-2-((1E,3S,4S)-3-hydroxy-4-methylnon-1-en-6-yn-1-yl)-5-oxocyclopentyl)heptanoic acid [Compound (1)-8]

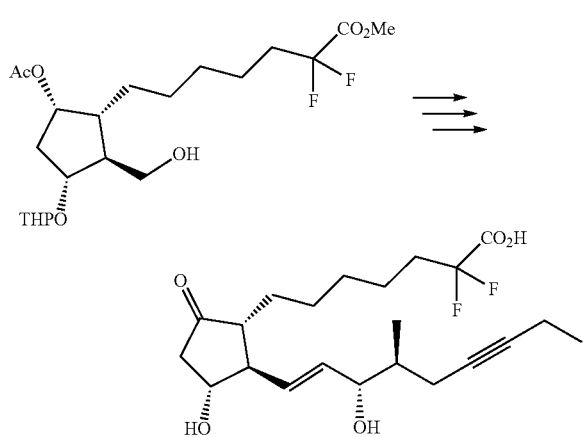

The title compound was synthesized in the same manner as in Reference Example 4—Reference Example 7 and Example 4 from methyl 7-((1R,2R,3R,5S)-5-acetoxy-2-hydroxymethyl-3-((tetrahydro-2H-pyran-2-yl)oxy)cyclopentyl)-2,2-difluoroheptanoate synthesized in Reference Example 11.

$^1$H NMR (400 MHz, CDCl$_3$) δ 5.60 (dddd, J=15.2, 15.2, 8.4, 7.4 Hz, 2H), 4.03 (dd, J=17.2, 8.4 Hz, 1H), 3.97 (t, J=7.6 Hz, 1H), 2.86-2.65 (m, 1H), 2.51-1.88 (m, 9H), 1.74 (m, 1H), 1.72-1.17 (m, 11H), 1.12 (t, J=7.4 Hz, 3H), 0.94 (d, J=6.8 Hz, 3H). $^{19}$F NMR (282.65 M Hz, CD$_3$OD) δ −106.42 (t, J=15.4 Hz, 2F).

Preparation Example 1: Production of Tablet

| | |
|---|---|
| 1) compound (1) | 0.003 g |
| 2) lactose | 50 g |
| 3) cornstarch | 15 g |
| 4) calcium carboxymethylcellulose | 44 g |
| 5) magnesium stearate | 1 g |
| 1000 tablets total | 110.003 g |

The total amount of 1), 2), and 3) and 30 g of 4) are kneaded with water, vacuum dried and sieved. The sieved powder is mixed with 14 g of 4) and 1 g of 5), and the mixture is punched by a tableting machine. In this manner, 1000 tablets containing 3 μg of the Example compound per tablet are obtained.

Preparation Example 2: Production of Capsule

| | |
|---|---|
| 1) compound (1) | 0.003 g |
| 2) fine powder cellulose | 10 g |
| 3) lactose | 19 g |
| 4) magnesium stearate | 1 g |
| total | 30.003 g |

1), 2), 3) and 4) are mixed and filled in gelatin capsules to give 1000 capsules containing 3 μg of the Example compound per capsule.

Experimental Example 1: Evaluation of Human Platelet Aggregation Inhibitory Action In Vitro (1) Preparation of Human Platelet-Rich Plasma Using 3.8 w/v % sodium citrate as an anticoagulant, blood samples were collected from human brachial vein at a ratio of sodium citrate solution:blood (volume ratio)=1:9, and an upper layer of platelet-rich plasma (PRP) was collected by centrifugation (120×g, 10 min). Platelet poor plasma (PPP) was prepared from PRP-free blood by centrifugation (1700× g, 10 min). The number of platelets in PRP was measured and adjusted to 25×10$^4$/μL by diluting with PPP.

(2) Measurement of Platelet Aggregation Ability

The platelet aggregation ability was measured by a platelet aggregometer (PRP313 M, IMI Co., Ltd.) according to the method of Born (Nature, 1962, vol. 194, pp. 927-929). PRP (190 μL) was placed in a glass cuvette and mounted on the platelet aggregometer. Then, 5 μL of the compound of the present invention, limaprost (positive control substance) or vehicle control (0.25 vol % dimethyl sulfoxide [DMSO]) was added as a test substance, and the mixture was incubated at 37° C. for 10 min. ADP (LMS Co., Ltd.) (5 μL) as a platelet aggregation agent was added at 3 µmol/L in a final concentration to cause aggregation, and the maximum response of the aggregation was measured.

(3) Evaluation of Inhibitory Action on Platelet Aggregation

The aggregation inhibition ratio of a test substance was determined by defining the maximum aggregation ratio of control as 100%, and $IC_{50}$ value was determined by using "Dx calculation (linear fitting): non-logit transformation" of SAS System Version 9.1.3 (Stat Preclinica Client Ver. 1.1 SAS Institute Japan, Ltd.). Furthermore, the relative activity (%) of each test substance was calculated by defining the activity of $IC_{50}$ value of limaprost as 100.

The results are shown in Table 1. As shown in Table 1, the compound of the present invention exhibited a very potent activity in the human platelet aggregation inhibitory action test in vitro, and some of them exhibited activity not less than 10-fold that of limaprost.

TABLE 1

| Test substance | Relative activity (%) |
| --- | --- |
| compound (1)-4 | 643 |
| compound (1)-5 | 161 |
| compound (1)-6 | 923 |
| compound (1)-7 | 1319 |
| compound (1)-9 | 1200 |
| compound (1)-10 | 1481 |
| limaprost | 100 |

Experimental Example 2: Evaluation of Inhibitory Action on Rat Platelet Aggregation In Vitro (1) Preparation of Rat Platelet-Rich Plasma In the same manner as in the above-mentioned Experimental Example 1(1), blood samples were collected from the abdominal artery of 8- to 9-week-old male SD rats. PRP was diluted with PPP and the number of platelet was adjusted to $63.2 \times 10^4$/µL.

(2) Measurement of Platelet Aggregation Ability

In the same manner as in the above-mentioned Experimental Example 1(2) except that the final concentration of ADP was 2 µmol/L, the compound of the present invention, prostaglandin E1 (PGE1:positive control substance) or vehicle control was added as a test substance, and the maximum response of aggregation was measured.

(3) Evaluation of Platelet Aggregation Inhibitory Action

In the same manner as in the above-mentioned Experimental Example 1(3), $IC_{50}$ values were determined from the aggregation inhibition ratio of the test substance, and the relative activity (%) of each test substance was calculated by defining the activity of $IC_{50}$ value of PGE1 as 100.

The results are shown in Table 2. The compound of the present invention showed a potent activity in the rat platelet aggregation inhibitory action test in vitro. All of compounds (1)-1 to (1)-3 as test substances are diastereomeric mixtures of R form and S form of the stereochemistry of the hydroxy group on the ω-chain. Therefore, when only the effective active form (one of the diastereomers) is separated from the mixture and the above-mentioned test is performed, the activity may be almost doubled.

TABLE 2

| Test substance | Relative activity (%) |
| --- | --- |
| compound (1)-1 | 169 |
| compound (1)-2 | 62 |
| compound (1)-3 | 2175 |

TABLE 2-continued

| Test substance | Relative activity (%) |
| --- | --- |
| compound (1)-8 | 817 |
| PGE1 | 100 |

Experimental Example 3: Evaluation of Persistent Inhibitory Action on Guinea Pig Platelet Aggregation Ex Vivo (1) Measurement of $IC_{50}$ Value As a test substance, a single oral dose of the compound of the present invention (3 doses of 79, 132 and 263 nmol/kg), limaprost (positive control substance: 3 doses of 79, 263 and 789 nmol/kg) or vehicle control (water for injection containing 0.26 vol % DMSO) was administered at 10 mL/kg to 4- to 10-week-old male Hartley guinea pigs. Blood samples were collected from the abdominal artery 4 hr later, platelet aggregation ability was measured, and the $IC_{50}$ value was calculated from the aggregation inhibitory activity (aggregation was induced by 0.5 µmol/L ADP) in the same manner as in the above-mentioned Experimental Example 1(3).

(2) Administration of Test Substance and Preparation of Platelet-Rich Plasma

A single oral dose showing the $IC_{50}$ value determined in the above-mentioned test (1) of compound (1)-7 (168 nmol/kg), compound (1)-9 (178 nmol/kg), compound (1)-10 (187 nmol/kg) or limaprost (266 nmol/kg) was administered. Blood samples were collected from the abdominal artery of the guinea pig at 1, 2, 4, 6, 10, 16 and 24 hr later. PRP was diluted with PPP and the number of platelet was adjusted to about $60 \times 10^4$/µL in the same manner as in the above-mentioned Experimental Example 1(1) (n=3–4).

(3) Measurement of Platelet Aggregation

In the same manner as in the above-mentioned Experimental Example 1(2), the platelet aggregation ability was measured according to the method of Born. PRP (190 µL) was placed in a glass cuvette, mounted on the platelet aggregometer and incubated at 37° C. for 10 min. ADP (10 µL) as platelet aggregation agent was added at 0.5 µmol/L in a final concentration to cause aggregation, and the maximum reaction of the aggregation was measured.

(4) Evaluation of Persistent Inhibitory Action on Platelet Aggregation

The maximum aggregation inhibition ratio of the test substance based on the maximum aggregation inhibition ratio of the control group as 0% was determined from the maximum coagulation ratio of the control group and the maximum coagulation ratio of the test substance when $IC_{50}$ values were calculated. Furthermore, in a graph showing time course changes of the maximum aggregation inhibition ratio, wherein the vertical axis shows the maximum aggregation inhibition ratio (%) and the horizontal axis shows time (hr) after administration of test substance, the area of the part surrounded by the line connecting the points of the maximum aggregation inhibition ratios plotted at each measurement time and the horizontal axis was determined as AUC. In addition, the assumed time at which the maximum aggregation inhibition ratio became 0% on the graph was determined as the time at which inhibition of aggregation disappeared (inhibition 0 hr).

The results are shown in Table 3. As shown in Table 3, in the guinea pig platelet aggregation inhibitory action test ex vivo, the compounds of the present invention showed higher AUC values from 1 hr after administration to inhibition 0 hr (AUC: 1-inhibition 0 hr) than limaprost did. It was confirmed that the compounds of the present invention had a more potent platelet aggregation inhibitory action than limaprost did. When the maximum aggregation inhibition ratio after 6 hr from the administration as an index of persistent activity was evaluated, the compounds of the present invention showed higher AUC values from 6 hr after administration to inhibition 0 hr (AUC: 6-inhibition 0 hr) and a longer time up to the disappearance of inhibitory of aggregation (inhibition 0 hr) in comparison with limaprost. It was therefore confirmed that the compounds of the present invention are superior to limaprost in the persistent efficacy.

TABLE 3

| Test substance | Inhibition 0 hr (hr) | AUC: 1-inhibition 0 hr (% relative to limaprost) | AUC: 6-inhibition 0 hr (% relative to limaprost) |
|---|---|---|---|
| compound (1)-7 | >24 | 713 (202) | 526 (359) |
| compound (1)-9 | 19.7 | 627 (178) | 401 (273) |
| compound (1)-10 | >24 | 719 (204) | 508 (346) |
| limaprost | 12.1 | 353 (100) | 147 (100) |

Experimental Example 4: Evaluation of Increasing Effect on rat Cauda Equine Blood Flow (1) Administration of Test Substance The compound of the present invention or limaprost (positive control substance) as a test substance was injected at 0.263, 0.789 and 2.63 nmol/kg in principle to Slc:Wistar male rats (body weight: about 200-250 g) from the tail vein at a flow rate of 0.2 mL/min for 10 min with an infusion pump (model 11, Harvard Apparatus). A vehicle (1 vol % DMSO-physiological saline) was similarly injected to the control group (5-6 mice in each group).

(2) Measurement of Cauda Equine Blood Flow

The rats were fixed in a prone position under halothane anesthesia and kept warm by a heater (Nippon Medical & Chemical Instruments Co., Ltd.). The lower back of the rats was shaved, dissected to expose the spine, the vertebral arch of the fifth lumbar vertebra was excised and cauda equina was exposed. The cauda equine blood flow was measured by a laser Doppler blood flow meter (TBF-LN1, Unique Medical Co., Ltd.) via a non-contact type probe (LP-NC special type, Unique Medical Co., Ltd.) fixed perpendicularly to a position of the exposed cauda equina upper by about 1 mm from before administration of each test substance until 60 min after the administration. The open wound was filled with liquid paraffin to prevent drying of the exposed cauda equina.

(3) Data Analysis

The obtained data was taken into a personal computer via PowerLab8/30 (registered trade mark, ML870, ADInstruments) every 1/400 second, and analyzed using LabChart (registered trade mark, ADInstruments). The analysis time points were before administration (administration 0 min), and 3, 5, 8, 10, 13, 15, 18, 20, 30, 40, 50 and 60 min after administration, or before administration (administration 0 min), and 3, 5, 10, 15, 20, 30, 40, 50 and 60 min after administration. The mean value for 10 seconds at each time point was taken as the measurement value, and the change rate (%) relative to the value before administration was obtained by the following equation.

The rate of change (%)=(measurement value at each time point after administration−measurement value before administration)/measurement value before administration×100

Furthermore, difference in the rate of change (%) relative to the control group at each time point [Δ change rate (%)] was calculated by the following equation, and the maximum value of the Δ change rate was taken as the maximum change rate.

Δchange rate (%)=change rate of each individual at each time point−mean of change rate of control group From the maximum change rate at each dose of the test substance, the dose at which the cauda equine blood flow increases by 20% ($ED_{20}$ value) was determined by linear regression equation, and the relative activity (%) of each test substance was calculated based on the activity of $ED_{20}$ value of limaprost as 100.

The results are shown in Table 4. The compounds of the present invention exhibited a potent activity in the rat cauda equine blood flow test.

TABLE 4

| Test substance | Relative activity (%) |
|---|---|
| compound (1)-4 | 147 |
| compound (1)-6 | 383 |
| compound (1)-7 | 375 |
| compound (1)-9 | 311 |
| compound (1)-10 | 550 |
| limaprost | 100 |

INDUSTRIAL APPLICABILITY

The prostaglandin derivative of the present invention is useful as an active ingredient of a medicament. A medicament containing the prostaglandin derivative of the present invention as an active ingredient is useful as a medicament for the prophylaxis or treatment of blood flow disorders, particularly, a medicament for the prophylaxis or treatment of a blood flow disorder associated with spinal canal stenosis or chronic arterial occlusion.

This application is based on a patent application No. 2016-094196 filed in Japan, the contents of which are incorporated in full herein.

The invention claimed is:

1. A compound, represented by formula (1) or a pharmaceutically acceptable salt thereof;

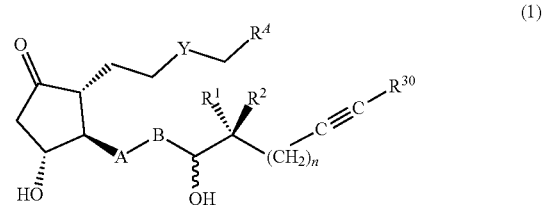

wherein
$R^A$ is —$CH_2$—$CZ^1Z^2$(COX) or —CH=$CZ^1$(COX),
$Z^1$ and $Z^2$ are each independently a hydrogen atom or a fluorine atom, X is $OR^4$ or $NR^5R^6$, $R^4$ is a hydrogen atom, an alkyl group having 1 to 6 carbon atoms or a substituted alkyl group having 1 to 6 carbon atoms, $R^5$ is a hydrogen atom, an alkyl group having 1 to 6 carbon atoms or a substituted alkyl group having 1 to 6 carbon atoms, $R^6$ is a hydrogen atom, an alkyl group having 1 to 6 carbon atoms, a substituted alkyl group having 1 to 6 carbon atoms, an alkylsulfonyl group having 1 to 6 carbon atoms, a substituted alkylsulfonyl group having 1 to 6 carbon atoms, an arylsulfonyl group having 6 to 10 carbon atoms or a substituted arylsulfonyl group having 6 to 10 carbon atoms;

Y is $CH_2$, S or O;

A-B is a carbon-carbon single bond or a carbon-carbon double bond;

a hydroxy group bonded by a wavy line is a hydroxy group having α-configuration, β-configuration or a mixed configuration of α-configuration and β-configuration;

$R^1$ and $R^2$ are each independently a hydrogen atom, an alkyl group having 1 to 3 carbon atoms or a substituted alkyl group having 1 to 3 carbon atoms;

n is an integer of 0 to 2; and $R^3$ is an alkyl group having 2 to 3 carbon atoms or a cycloalkyl group having 3 to 5 carbon atoms.

2. The compound or pharmaceutically acceptable salt of claim 1, wherein Y is $CH_2$.

3. The compound or pharmaceutically acceptable salt of claim 1, wherein $R^4$ is —CH=$CZ^1$(COX).

4. The compound or pharmaceutically acceptable salt of claim 1, wherein $R^4$ is —$CH_2$—$CZ^1Z^2$(COX).

5. The compound or pharmaceutically acceptable salt of claim 1, wherein n is 1.

6. The compound or pharmaceutically acceptable salt of claim 1, wherein A-B is a carbon-carbon double bond.

7. The compound or pharmaceutically acceptable salt of claim 1, wherein $R^1$ is a hydrogen atom and $R^2$ is an alkyl group having 1 to 3 carbon atoms.

8. The compound or pharmaceutically acceptable salt of claim 1, wherein $R^3$ is a cycloalkyl group having 3 to 5 carbon atoms.

9. The compound or pharmaceutically acceptable salt of claim 1, wherein X is $OR^4$.

10. A cyclodextrin clathrate compound, comprising the compound or pharmaceutically acceptable salt of claim 1.

11. A medicament, comprising the compound or pharmaceutically acceptable salt of claim 1.

12. A method of treating a blood flow disorder, the method comprising administering the medicament of claim 11, as a prophylactic or therapeutic agent, to a subject in need thereof.

13. The method of claim 12, wherein the blood flow disorder is a blood flow disorder of a nerve.

14. The method of claim 13, wherein the blood flow disorder of the nerve is a blood flow disorder associated with spinal canal stenosis.

15. The method of claim 12, wherein the blood flow disorder is a blood flow disorder of a peripheral artery, skin or brain.

16. The method of claim 15, wherein the blood flow disorder is a blood flow disorder of a peripheral artery that is a blood flow disorder associated with chronic arterial occlusion or pulmonary hypertension.

17. The method of claim 15, wherein the blood flow disorder is a blood flow disorder of skin that is a blood flow disorder associated with a pressure ulcer.

18. The method of claim 15, wherein the blood flow disorder is a blood flow disorder of brain that is a blood flow disorder associated with a suppression of recurrence after a cerebral infarction.

19. A medicament, comprising the cyclodextrin clathrate compound of claim 10.

20. A method of treating a blood flow disorder, the method comprising administering the medicament of claim 19, as a prophylactic or therapeutic agent, to a subject in need thereof.

* * * * *